(12) United States Patent
Khairkhahan et al.

(10) Patent No.: US 8,257,428 B2
(45) Date of Patent: Sep. 4, 2012

(54) SYSTEM FOR IMPROVING CARDIAC FUNCTION

(75) Inventors: Alexander Khairkhahan, Palo Alto, CA (US); Hugh R. Sharkey, Redwood City, CA (US); Serjan D. Nikolic, San Francisco, CA (US)

(73) Assignee: CardioKinetix, Inc., Menlo Park, CA (US)

( * ) Notice: Subject to any disclaimer, the term of this patent is extended or adjusted under 35 U.S.C. 154(b) by 2922 days.

(21) Appl. No.: 10/436,959

(22) Filed: May 12, 2003

(65) Prior Publication Data

US 2006/0264980 A1 Nov. 23, 2006

Related U.S. Application Data

(63) Continuation-in-part of application No. 10/212,033, filed on Aug. 1, 2002, which is a continuation-in-part of application No. 09/635,511, filed on Aug. 9, 2000, now abandoned.

(60) Provisional application No. 60/147,894, filed on Aug. 9, 1999.

(51) Int. Cl.
*A61F 2/06* (2006.01)
(52) U.S. Cl. ........... 623/1.23; 600/16; 600/37; 606/200; 604/508
(58) Field of Classification Search .......... 600/16, 600/37, 375; 604/508; 606/200, 213, 232; 623/23.67, 3.16, 1.11
See application file for complete search history.

(56) References Cited

U.S. PATENT DOCUMENTS

| | | |
|---|---|---|
| 3,874,388 A | 4/1975 | King et al. |
| 4,007,743 A | 2/1977 | Blake |
| 4,425,908 A | 1/1984 | Simon |
| 4,619,246 A | 10/1986 | Molgaard-Nielsen et al. |
| 4,685,446 A | 8/1987 | Choy |
| 4,710,192 A | 12/1987 | Liotta et al. |
| 4,832,055 A | 5/1989 | Palestrant |
| 4,917,089 A | 4/1990 | Sideris |
| 5,104,399 A | 4/1992 | Lazarus |
| 5,192,301 A | 3/1993 | Kamiya et al. |
| 5,192,314 A | 3/1993 | Daskalakis |
| 5,375,612 A | 12/1994 | Cottenceau et al. |

(Continued)

FOREIGN PATENT DOCUMENTS

WO   WO 00/27292   5/2000

(Continued)

OTHER PUBLICATIONS

Khairkhahan, et al., U.S. Appl. No. 11/151,164, entitled "Peripheral seal for a ventricular partitioning device," filed Jun. 10, 2005.

(Continued)

*Primary Examiner* — Vy Q Bui
(74) *Attorney, Agent, or Firm* — Shay Glenn LLP

(57) ABSTRACT

A system for improving cardiac function is provided. A foldable and expandable frame having at least one anchoring formation is attached to an elongate manipulator and placed in a catheter tube while folded. The tube is inserted into a left ventricle of a heart where the frame is ejected from the tube and expands in the left ventricle. Movements of the elongate manipulator cause the anchor to penetrate the heart muscle and the elongate manipulator to release the frame. The installed frame minimizes the effects of an akinetic portion of the heart forming an aneurysmic bulge.

1 Claim, 33 Drawing Sheets

U.S. PATENT DOCUMENTS

| | | | |
|---|---|---|---|
| 5,385,156 A | 1/1995 | Oliva |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |
| 5,549,621 A | 8/1996 | Bessler et al. |
| 5,578,069 A | 11/1996 | Miner, II |
| 5,634,936 A | 6/1997 | Linden et al. |
| 5,634,942 A | 6/1997 | Chevillon et al. |
| 5,702,343 A | 12/1997 | Alferness |
| 5,709,707 A | 1/1998 | Lock et al. |
| 5,791,231 A | 8/1998 | Cohn et al. |
| 5,797,849 A | 8/1998 | Vesely et al. |
| 5,797,960 A | 8/1998 | Stevens et al. |
| 5,829,447 A | 11/1998 | Stevens et al. |
| 5,833,698 A | 11/1998 | Hinchliffe et al. |
| 5,836,968 A | 11/1998 | Simon et al. |
| 5,843,170 A | 12/1998 | Ahn |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,045,497 A | 4/2000 | Schweich et al. |
| 6,059,715 A | 5/2000 | Schweich et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,152,144 A * | 11/2000 | Lesh et al. ............ 128/898 |
| 6,156,027 A | 12/2000 | West |
| 6,161,543 A | 12/2000 | Cox et al. |
| 6,193,731 B1 | 2/2001 | Oppelt et al. |
| 6,221,092 B1 | 4/2001 | Koike et al. |
| 6,231,561 B1 | 5/2001 | Frazier et al. |
| 6,258,021 B1 | 7/2001 | Wilk |
| 6,267,772 B1 | 7/2001 | Mulhauser et al. |
| 6,290,674 B1 | 9/2001 | Roue et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,228 B1 | 11/2002 | Norred |
| 6,506,204 B2 | 1/2003 | Mazzocchi |
| 6,511,496 B1 | 1/2003 | Huter et al. |
| 6,537,198 B1 | 3/2003 | Vidlund et al. |
| 6,547,821 B1 | 4/2003 | Taylor et al. |
| 6,551,303 B1 | 4/2003 | Van Tassel et al. |
| 6,592,608 B2 | 7/2003 | Fisher et al. |
| 6,652,555 B1 | 11/2003 | VanTassel et al. |
| 6,685,627 B2 | 2/2004 | Jayaraman |
| 6,852,076 B2 | 2/2005 | Nikolic et al. |
| 6,959,711 B2 | 11/2005 | Murphy et al. |
| 6,994,093 B2 | 2/2006 | Murphy et al. |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0111647 A1 | 8/2002 | Khairkhahan et al. |
| 2002/0133227 A1 | 9/2002 | Murphy et al. |
| 2002/0161394 A1 | 10/2002 | Macoviak et al. |
| 2002/0169359 A1 | 11/2002 | McCarthy et al. |
| 2002/0169360 A1 | 11/2002 | Taylor et al. |
| 2002/0188170 A1 | 12/2002 | Santamore et al. |
| 2003/0045896 A1 | 3/2003 | Murphy et al. |
| 2003/0050682 A1 | 3/2003 | Sharkey et al. |
| 2003/0050685 A1 | 3/2003 | Nikolic et al. |
| 2003/0105384 A1 | 6/2003 | Sharkey et al. |
| 2003/0109770 A1 | 6/2003 | Sharkey et al. |
| 2003/0120337 A1 | 6/2003 | Van Tassel et al. |
| 2003/0149333 A1 | 8/2003 | Alferness |
| 2003/0149422 A1 | 8/2003 | Muller |
| 2003/0220667 A1 | 11/2003 | Van Der Burg et al. |
| 2004/0002626 A1 | 1/2004 | Feld et al. |
| 2004/0034366 A1 | 2/2004 | van der Burg et al. |
| 2004/0044361 A1 | 3/2004 | Frazier et al. |
| 2004/0064014 A1 | 4/2004 | Melvin et al. |
| 2005/0096498 A1 | 5/2005 | Houser et al. |
| 2005/0154252 A1 | 7/2005 | Sharkey et al. |
| 2005/0177180 A1 | 8/2005 | Kaganov et al. |
| 2005/0197716 A1 | 9/2005 | Sharkey et al. |
| 2005/0216052 A1 | 9/2005 | Mazzocchi et al. |
| 2006/0014998 A1 | 1/2006 | Sharkey et al. |
| 2006/0025800 A1 | 2/2006 | Suresh |
| 2006/0030881 A1 | 2/2006 | Sharkey et al. |

FOREIGN PATENT DOCUMENTS

| | | |
|---|---|---|
| WO | WO 01/30266 | 5/2001 |
| WO | WO 01/78625 | 10/2001 |
| WO | WO 02/30335 | 4/2002 |
| WO | WO 02/071977 A2 | 9/2002 |
| WO | WO 03/007778 A | 1/2003 |
| WO | WO 2004/012629 A | 2/2004 |
| WO | WO 2004/100803 | 11/2004 |
| WO | WO 2005/007031 | 1/2005 |

OTHER PUBLICATIONS

Sharkey, et al., U.S. Appl. No. 11/199,633, entitled "Method for treating myocardial rupture," filed Aug. 9, 2005.

Khairkhahan, et al; U.S. Appl. No. 11/801,075, entitled "System for improving cardiac function," filed May 7, 2007.

Khairkhahan et al; U.S. Appl. No. 11/800,998, entitled "System for improving cardiac function," filed May 7, 2007.

Nikolic et al; U.S. Appl. No. 11/640,469, entitled "Cardiac device and methods of use thereof," filed Dec. 14, 2006.

International Search Report and Written Opinion for PCT/US2005/000264 mailed Apr. 26, 2005.

International Search Report and Written Opinion for PCT/US2004/014782 mailed Sep. 21, 2004.

Khairkhahan et al; U.S. Appl. No. 11/860,438 entitled "Laminar ventricular partitioning device," filed Sep. 24, 2007.

Nikolic, et al., U.S. Appl. No. 12/129,443 entitled "Therapeutic methods and devices following myocardial infarction," filed May 29, 2008.

Khairkhahan et al; U.S. Appl. No. 12/125,015 entitled "Ventricular partitioning device," filed May 21, 2008.

Khairkhahan et al; U.S. Appl. No. 11/060,438 entitled "Laminar ventricular partitioning device," filed Sep. 24, 2007.

AGA Medical Corporatioin. www.amplatzer.com/products. "The Muscular VSD Occluder" and "The Septal Occluder" device description. Accessed Apr. 3, 2002.

Di Mattia, et al. Surgical treatment of left ventricular post-infarction aneurysm with endoventriculoplasty: late clinical and functioal results. European Journal of Cardio-thoracic Surgery. 1999; 15:413-418.

Dor, et al. Ventricular remodeling in coronary artery disease. Current Opinion in Cardiology. 1997; 12:533-537.

Dor, V. The treatment of refractory ischemic ventricular tachycardia by endoventricular patch plasty reconstruction of the left ventricle. Seminars in Thoracic and Cardiovascular Surgery. 1997; 9(2): 146-155.

DOR. Surgery for left ventricular aneurysm. Current Opinion in Cardiology. 1990; 5: 773-780.

Gore Medical. www.goremedical.com. "Helex Septal Occluder" product description. Accessed Apr. 3, 2002.

Katsumata, et al. An objective appraisal of partial left ventriculectomy for heart failure. Journal of Congestive Hear Failure and Circulator Support. 1999; 1(2): 97-106.

Kawata, et al. Systolic and Diastolic Function after Patch Reconstruction of Left Ventricular Aneurysms. Ann. Thorac. Surg. 1995; 59:403-407.

\* cited by examiner

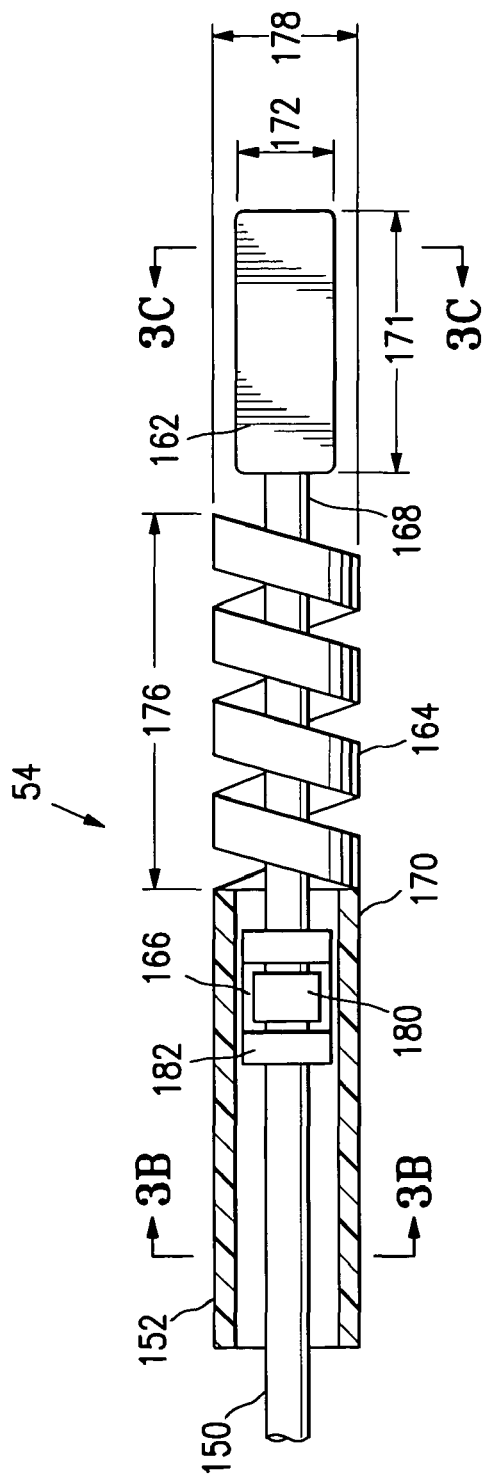
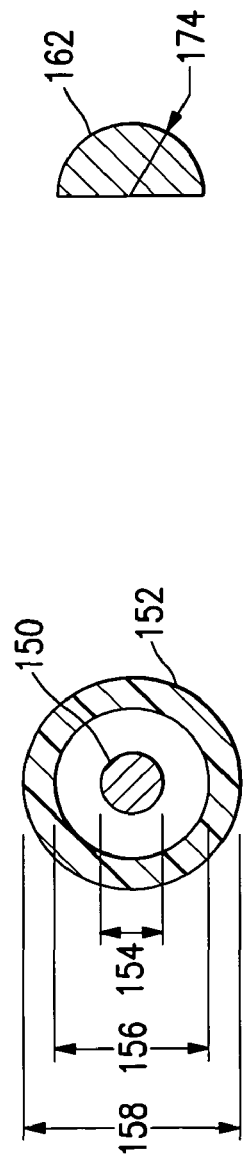
FIG. 3A
FIG. 3B
FIG. 3C

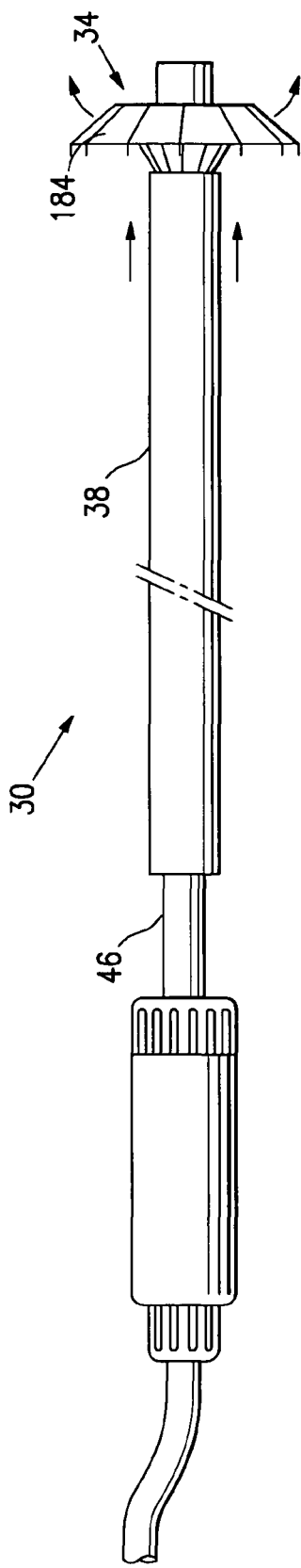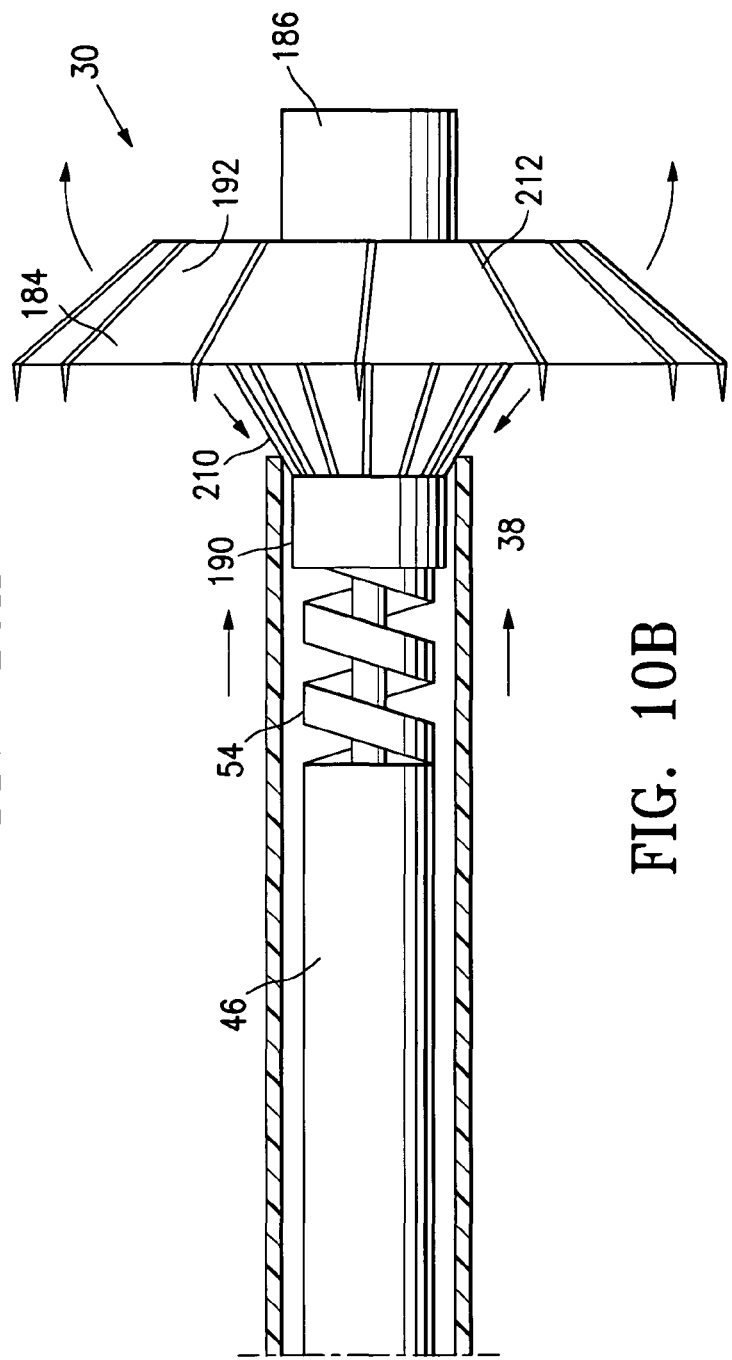
FIG. 10A
FIG. 10B

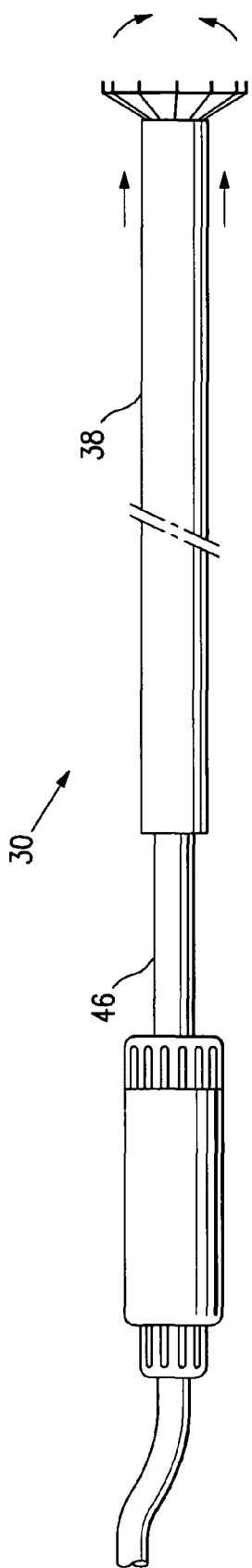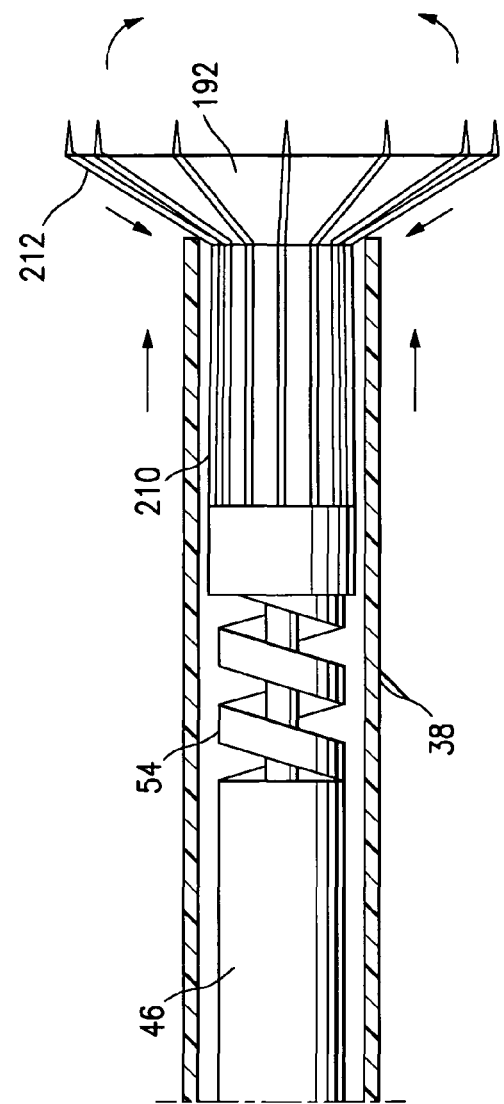
FIG. 11A
FIG. 11B

SYSTEM FOR IMPROVING CARDIAC FUNCTION

CROSS REFERENCE TO RELATED APPLICATIONS

This is a continuation-in-part of U.S. patent application Ser. No. 10/212,033, filed on Aug. 1, 2002, which is a continuation-in-part of prior U.S. patent application Ser. No. 09/635,511, filed on Aug. 9, 2000, now abandoned, which claims priority from U.S. Provisional Patent Application No. 60/147,894, filed on Aug. 9, 1999, and are incorporated herein by reference in their entirety.

BACKGROUND OF THE INVENTION

1. Field of the Invention

Embodiments of this invention relate to a method and device for improving cardiac function.

2. Discussion of Related Art

Congestive heart failure annually leads to millions of hospital visits internationally. Congestive heart failure is the description given to a myriad of symptoms that can be the result of the heart's inability to meet the body's demand for blood flow. In certain pathological conditions, the ventricles of the heart become ineffective in pumping the blood, causing a back-up of pressure in the vascular system behind the ventricle.

The reduced effectiveness of the heart is usually due an enlargement of the heart. A myocardial ischemia may, for example, cause a portion of a myocardium of the heart to lose its ability to contract. Prolonged ischaemia can lead to infarction of a portion of the myocardium (heart muscle) wherein the heart muscle dies and becomes scar tissue. Once this tissue dies it no longer functions as a muscle and cannot contribute to the pumping action of the heart. When the heart tissue is no longer pumping effectively, that portion of the myocardium is said to be hypokinetic, meaning that it is less contractile than the uncompromised myocardial tissue. As this situation worsens, the local area of compromised myocardium may in fact bulge out as the heart contracts, further decreasing the heart's ability to move blood forward. When local wall motion moves in this way, it is said to be dyskinetic, or akinetic. The dyskinetic portion of the myocardium may stretch and eventually form an aneurysmic bulge. Certain diseases may cause a global dilated myopathy, i.e., a general enlargement of the heart when this situation continues for an extended period of time.

As the heart begins to fail, distilling pressures increase, which stretches the ventricular chamber prior to contraction and greatly increases the pressure in the heart. In response, the heart tissue reforms to accommodate the chronically increased filling pressures, further increasing the work that the now comprised myocardium must perform.

This vicious cycle of cardiac failure results in the symptoms of congestive heart failure, such as shortness of breath on exertion, edema in the periphery, nocturnal dypsnia (a characteristic shortness of breath that occurs at night after going to bed), waking, and fatigue, to name a few. The enlargements increase stress on the myocardium. The stress increase requires a larger amount of oxygen supply, which can result in exhaustion of the myocardium leading to reduced cardiac output of the heart.

SUMMARY OF THE INVENTION

The invention provides an apparatus for improving cardiac function comprising at least one external actuator, an elongate manipulator connected to the external actuator, a manipulator-side engagement component on a distal end of the elongate manipulator, a collapsible and expandable frame, a frame-side engagement component releasably engageable with the manipulator side-engagement component so that the external actuator can steer the frame when collapsed into a ventricle of a heart whereafter the frame is expanded, and at least one anchor connected to the frame, movement of the external actuator allowing for (i) insertion of the anchor and (ii) a myocardium ventricle, (iii) subsequent withdrawal of the anchor of the myocardium, (iv) subsequent reinsertion of the anchor into the myocardium, said insertion securing the frame to the myocardium in a selected position, and (v) subsequent disengagement of the manipulator-side engagement component from the frame-side engagement component, said disengagement for releasing the frame from the elongate manipulator.

The frame may have a small cross-dimension when collapsed suitable for being inserted into the ventricle of the heart through a tubular passage in a large cross-dimension when expanded in the ventricle.

The frame may comprise plurality of segments extending from a central portion of the frame.

The frame may be made of nickel titanium or stainless steel.

The apparatus may further comprise a membrane stretched between the segments, the membrane dividing the ventricle into at least two volumes. The membrane may be made of ePTFE. The membrane may be a mesh.

The segments may further comprise first and second portions connected at ends thereof such that the second portions are at an angle to the first portions.

The frame may have proximal and distal sections. The frame may have a diameter of between 10 mm and 100 mm when expanded.

The apparatus may further comprise at least one active anchor and at least one passive anchor. Said insertion of the passive anchor may be in a first direction and said withdrawal of the passive anchor may be in a second direction, the second direction being substantially 180 degrees from the first direction.

The apparatus may further comprise a first passive anchor extending in the first direction and a second passive anchor extending in a third direction. The active and passive anchors may have sharp ends that penetrate the myocardium.

The apparatus may further comprise a tubular passage with a distal end suitable to be inserted into the ventricle.

The elongate manipulator may further comprise a frame member with proximal and distal ends and an anchor member with proximal and distal ends, the frame and anchor members being moveable through the tubular passage.

The manipulator side-engagement component may further comprise a frame formation on the distal end of the frame member and an anchoring formation on the distal end of the anchor member.

The apparatus may further comprise an external frame actuator connected to the proximal end of the frame member and an external anchor actuator connected to the proximal end of the anchor member.

When the distal end of the elongate manipulator is in the selected position, a first movement of the external anchor actuator may cause the active anchor to be inserted into the myocardium to secure the frame to the myocardium and a second movement of the external anchor actuator may cause the active anchor to withdraw from the myocardium, said withdrawal releasing the frame from the myocardium.

A first movement of the external frame actuator may cause the frame formation to engage the frame-side engagement component, said engagement securing the frame to the distal end of the elongate manipulator and a second movement of the external frame actuator may cause the frame formation to disengage the frame-side engagement component, said disengagement releasing the frame from the elongate manipulator.

The frame may be shaped such that entry of the proximal section of the frame into the tubular passage causes the frame to partially collapse such that the passive anchor withdraws from the myocardium in the second direction and entry of the distal section of the frame into the tubular passage causes the frame to collapse to the small cross-section so that the distal end of the elongate manipulator and the frame can be removed from the heart.

The elongate manipulator and the frame may be insertable into the heart simultaneously and the frame may be shaped such that exposure of the distal section of the frame from the distal end of the tubular passage allows the frame to partially expand and exposure of the proximal section of the frame from the distal end of the tubular passage allows the frame to expand to a large cross-section, said expansion causing the passive anchors to penetrate the myocardium to secure the frame to the myocardium.

The invention also provides an apparatus for improving cardiac function comprising a frame which includes a plurality of central segments surrounding a central axis, the central segments having first and second ends, the first ends being pivotally connected to one another, and a plurality of outer segments having first and second ends, the first ends being pivotally secured to the second ends of the central segments, a membrane secured to the frame such that movement of the second ends of the central segments away from the central axis causes the membrane to unfold, the unfolding of the membrane causing the outer segments to pivot relative to the respective central segments away from the central axis and movement of the second ends of the central segments toward the central axis causes the membrane to fold, the folding of the membrane causing the outer segments to pivot relative to their respective central segments toward the central axis, and an anchor connected to the frame, the anchor being insertable into a myocardium of a heart to secure the cardiac device to the myocardium in a ventricle of the heart.

The frame may include at least three central segments and at least three outer segments.

The membrane may be stretched between the central and the outer segments.

The anchor may be secured directly to the frame.

The invention further provides an apparatus for improving cardiac function comprising a frame, a membrane, having an inner surface, secured to the frame, the membrane and the frame jointly forming a cardiac device being moveable between a collapsed and an expanded state, in a collapsed state at least a portion of the inner surface of the membrane facing a vertical axis of the cardiac device and the cardiac device being insertable into a ventricle of a heart, in the expanded state the portion of the inner surface of the membrane facing away from the vertical axis and being in contact with a myocardium and the cardiac device being in a selected position in the ventricle, and an anchor connected to the cardiac device, the anchor being insertable into the myocardium of the heart to secure the cardiac device to the myocardium in the selected position in the ventricle.

The cardiac device may collapse toward the vertical axis and expand away from the vertical axis.

The membrane may fold towards the vertical axis when the cardiac device collapses and may unfold away from the vertical axis when the cardiac device expands.

The frame may be at least one of nickel titanium and stainless steel.

The membrane may be made of ePTFE.

The anchor may have a sharp end.

The invention further provides an apparatus for improving cardiac function comprising a frame being expandable in a selected position to a pre-set shape in a ventricle of a heart, a formation on the frame, and an anchoring device having an anchor, the anchoring device being engaged with and rotatable relative the formation to rotate the anchor relative to the frame, said rotation causing the anchor to be inserted into a myocardium of the heart, said insertion securing the frame in the selected position in the ventricle.

The anchoring device may engage the formation such that a first rotation of the anchoring device causes the anchor to move away from the frame and a second rotation of the anchoring device causes the anchor to move toward the frame.

The formation may be a pin, and the anchor may be a screw.

The invention further provides an apparatus for improving cardiac function comprising at least a primary expandable frame being in a selected position in a ventricle of a heart when expanded, an anchor connected to the frame, the anchor being insertable into a myocardium of the heart to secure the primary frame within the ventricle, a frame-side engagement component connected to the primary frame, a membrane, and a membrane-side engagement component being engageable with the frame-side engagement component, said engagement securing the membrane to the frame.

The apparatus may further comprise a secondary expandable frame being in a selected position in the ventricle of the heart when expanded, the secondary frame being secured to the membrane and connected to the membrane-side engagement component thereby interconnecting the membrane to the membrane-side engagement component.

The anchor may be connected to the at least one frame.

The frame-side engagement component may be connected to the primary frame at a central portion of the primary frame.

The membrane-side engagement component may be connected to the secondary frame at a central portion of the secondary frame.

The apparatus may further comprise an active anchor being connected to the frame-side engagement component such that a first movement of the frame-side engagement component causes the active anchor to enter the myocardium and a second movement of the frame-side engagement component causes the active anchor to withdraw from the myocardium.

The apparatus may further comprise a passive anchor being connected to at least one of the frames such that the passive anchor enters the myocardium when the frame expands.

The invention further provides an apparatus for improving cardiac function comprising a flexible liner, a membrane secured to the liner, the membrane and the liner jointly forming a cardiac device being moveable between a collapsed and an expanded state, in the collapsed state the cardiac device being insertable into a ventricle of a heart. In the expanded state the cardiac device being in a selected position in the ventricle, the liner covering a wall in the ventricle and the membrane separating the ventricle into two volumes, and an anchor connected to the cardiac device, the anchor being insertable into a myocardium of the heart to secure the cardiac device to the myocardium in the selected position in the ventricle.

The flexible liner may comprise a plurality of lengths of strands being connected at endpoints thereof.

The apparatus may further comprise a frame secured to the cardiac device and connected to the anchor thereby interconnecting the cardiac device and the anchor.

The apparatus may further comprise a frame-side engagement component being connected to the cardiac device and an active anchor being connected to the frame-side engagement component such that a first movement of the frame-side engagement component causes the active anchor to enter the myocardium and a second movement of the frame-side engagement component causes the active anchor to withdraw from the myocardium.

The apparatus may further comprise a passive anchor being connected to the cardiac device such that the passive anchor enters the myocardium when the cardiac device expands.

The invention further provides an apparatus for improving cardiac function comprising an expandable frame being in a selected position in a ventricle of the heart and having an outer edge when expanded, the outer edge defining a non-planar cross-section of an inner wall of a ventricle and an anchor connected to the frame, the anchor being insertable into the myocardium of the heart to secure the frame to the myocardium in the selected position in the ventricle.

The apparatus may further comprise a membrane being secured to a frame, the membrane separating the ventricle into two volumes.

The frame may have a vertical axis and the outer edge may have a diameter, the diameter intersecting the vertical axis at an angle other than 90 degrees.

The invention further provides an apparatus for improving cardiac function comprising an anchor being insertable into a myocardium of a heart to secure the anchor to the myocardium within a ventricle of the heart, an anchor-side engagement component being secured to the anchor, an expandable frame being in a selected position in the ventricle when expanded, and a frame-side engagement component being secured to the frame, the frame-side engagement component being engageable with the anchor-side engagement component, said engagement securing the frame to the anchor in the selected position in the ventricle.

The apparatus may further comprise a membrane being secured to the frame.

A first movement of the anchor-side engagement component may cause the anchor to enter a myocardium and a second movement of the anchor-side engagement component may cause the anchor to withdraw from the myocardium.

A first movement of the frame-side engagement component may cause the frame-side engagement component to engage the anchor-side engagement component and a second movement of the frame-side engagement component may cause the frame-side engagement component to disengage the anchor-side engagement component.

Said engagement may release the frame from the anchor.

The invention further provides an apparatus for improving cardiac function comprising a flexible body, a membrane connected to the flexible body, the membrane and flexible body jointly forming a cardiac device being movable between a collapsed and an expanded state, in the collapsed state the cardiac device being insertable into a ventricle of the heart, in the expanded state the cardiac device being in a selected position in the ventricle, and an anchor connected to the cardiac device, the anchor being insertable into the myocardium of the heart to secure the cardiac device to the myocardium in the selected position of the ventricle.

The apparatus may further comprise a frame having a distal end, the membrane may be secured to the frame, and the body may have proximal and distal ends, the proximal end of the body being secured to the distal end of the frame, and the distal end of the body being connected to the anchor.

The body may be cylindrical with a diameter of between 0.5 mm and 6 mm and a height of between 1 mm and 100 mm.

The cardiac device may have a vertical axis.

The body may have a proximal opening at the proximal end, a distal opening at the distal end, and a passageway therethrough connecting the proximal and distal openings.

The body may be able to bend between 0 and 120 degrees from the vertical axis.

The invention further provides a device for improving cardiac function comprising a collapsible and expandable frame having first and second portions, the frame being insertable into a ventricle of a heart when collapsed, when expanded the frame being in a selected position in the ventricle and the second portion of the frame covering a wall in the ventricle, a membrane secured to the frame such that the membrane divides the ventricle into at least two volumes when the frame is expanded, the frame and the membrane jointly forming a cardiac device, and an anchor connected to the cardiac device, the anchor being insertable into a myocardium of the heart to secure the cardiac device in the selected position in the ventricle.

The frame may further comprise a plurality of segments, each segment having an inner and outer portion being connected at ends thereof, the outer portions being at an angle to the inner portions.

The membrane may be secured to the inner and outer portions of the segments.

The device may further comprise a plurality of anchors being connected to at least one segment such that when the frame expands the anchors enter the myocardium in a first direction, and when the frame collapses the anchors withdraw from the myocardium in a second direction approximately 180 degrees from the first direction.

Some of the anchors may extend in a third direction.

The invention further provides a system for improving cardiac function comprising a collapsible and expandable frame, when collapsed the frame being insertable into a selected position in a ventricle of the heart through an opening in the heart having a small cross-dimension, when expanded in the selected position, the frame having a large cross-dimension, and an anchor connected to the frame, being insertable into a myocardium of the heart to secure the frame to the myocardium in the selected position.

The opening may be an incision in the myocardium.

The anchor may further comprise a plurality of strands woven through the myocardium such that the opening is closed.

The invention further provides a system for improving cardiac function comprising an external actuator, an elongate manipulator having a tube suitable to be inserted into a ventricle of a heart to a selected position and a deployment member positioned therein slidable between a first and second position, the deployment member having proximal and distal ends, the distal end being within the tube when the deployment member is in the first position and out of the tube when the deployment member is in the second position, the deployment member being connected to the external actuator at the proximal end thereof, a deployment-side engagement component on the distal end of the deployment member, a frame-side engagement component being engageable with the deployment-side engagement component, said engagement securing the deployment-side engagement component to the frame-side engagement component such that a movement of the external actuator causes the engagement components to disengage, said disengagement releasing the deployment-side engagement component from the frame-side engagement component, a frame being connected to the frame-side engagement component, the frame being moveable between a collapsed and an expanded state, the frame being connected to the deployment member in the collapsed state with a small cross-dimension when the deployment member is in the first position and the frame is within the tube, the frame being shaped such that when the deployment member is moved to the second position and the frame exits the tube, the frame expands to the expanded state with a large cross-dimension and when the deployment member is moved back to the first position, the frame collapses to the collapsed state as the frame enters the tube, and an anchor connected to the frame being insertable into a myocardium of the heart to secure the frame to the myocardium of the heart, such that the deployment mechanism can be removed from the heart, the anchor entering the myocardium in a first direction when the frame expands and withdrawing from the myocardium in a second direction when the frame collapses, said withdrawal releasing the frame from the myocardium.

The external manipulator may further comprise an anchor deployment knob and a detachment knob.

The deployment member may further comprise an anchor shaft having proximal and distal ends and a detachment shaft having proximal and distal ends, the proximal end of the anchor shaft being connected to the anchor deployment knob, the proximal end of the detachment shaft being connected to the detachment knob.

The deployment-side engagement component may further comprise a deployment-side anchor formation connected to the distal end of the anchor shaft and a deployment-side detachment formation connected to the distal end of the detachment shaft.

The frame-side engagement component may further comprise a frame-side anchor formation being connected to the anchor and a frame-side detachment formation on the frame, the frame-side anchor formation being engageable with the deployment-side anchor formation, the frame-side detachment formation being engageable with the deployment-side detachment formation, a first movement of the detachment knob causing the deployment-side detachment formation to engage the frame-side detachment formation, said engagement securing the frame to the deployment member, a first movement of the anchor deployment knob causing the anchor to enter the myocardium and a second movement of the anchor deployment knob causing the anchor to withdraw from the myocardium, a second movement of the detachment knob causing the deployment-side detachment formation to disengage the frame-side detachment formation, said disengagement releasing the frame from the deployment member.

The anchor shaft and the detachment shaft may be coaxial.

The anchor shaft may be an inner torque shaft and the detachment shaft may be an outer torque shaft.

BRIEF DESCRIPTION OF THE DRAWINGS

The invention is further described by way of examples with reference to the accompanying drawings, wherein:

FIG. 3A is cross-sectional side view of a distal end of the deployment member including a key and a detachment screw;

FIG. 3B is a cross-sectional end view on 3B-3B in FIG. 3A of the deployment member;

FIG. 3C is a cross-sectional end view on 3C-3C in FIG. 3A of the key;

FIG. 10A is a view similar to FIG. 9 with the cardiac device partially retracted into the catheter;

FIG. 10B is a cross-sectional side view of a portion of FIG. 10A;

FIG. 11A is a side view of the system with the cardiac device further retracted;

FIG. 11B is a cross-sectional side view of a portion of FIG. 11A;

DETAILED DESCRIPTION OF THE INVENTION

Figure 1:
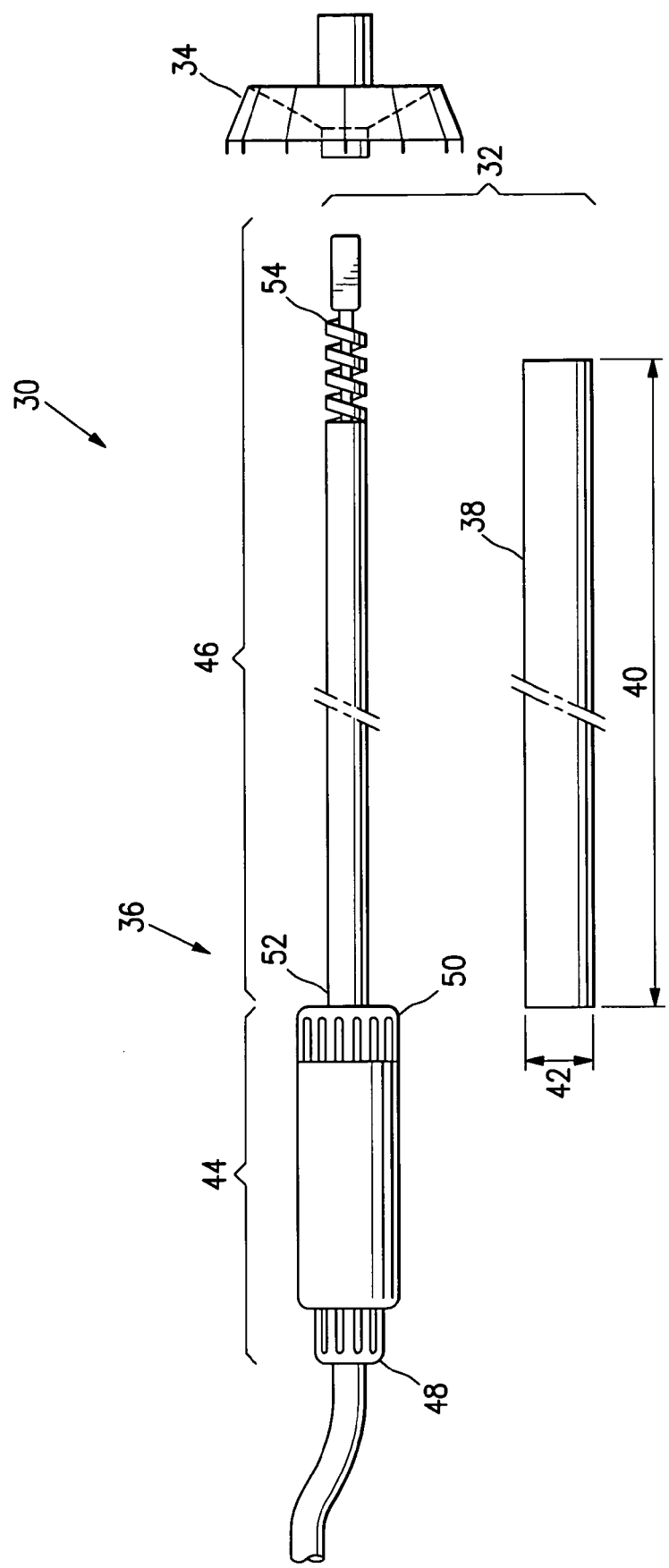
FIG. 1 is an exploded side view of a system for improving cardiac function, according to one embodiment of the invention, including a cardiac device and a deployment system, the deployment system including a deployment mechanism and a catheter tube.

FIG. 1 illustrates a system 30 for improving cardiac function according to one embodiment of the invention. The system 30 includes a deployment system 32 and a cardiac device 34. The deployment system 32 includes a deployment mechanism 36 and a catheter tube 38.

The catheter tube 38 is cylindrical with a length 40 of 110 cm and a diameter 42 of 5 mm. The catheter tube 38 has a circular cross-section and is made of a soft, flexible material.

The deployment mechanism 36 includes a handle 44 and a deployment member 46. The handle 44 has a proximal end 48 and a distal end 50. The deployment member 46 has a proximal end 52 and a distal end 54. The proximal end 52 of the deployment member 46 is secured to the distal end 50 of the handle 44.

Figure 2:
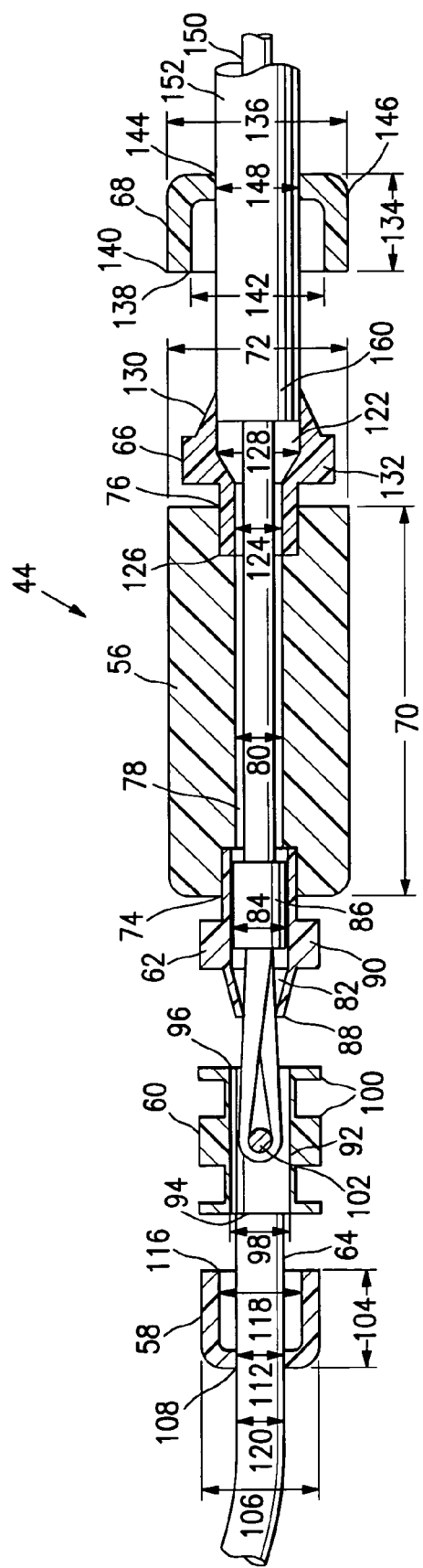
FIG. 2 is a cross-sectional side view of a handle of the deployment mechanism and a proximal end of a deployment member of the deployment mechanism.
Figure 4:
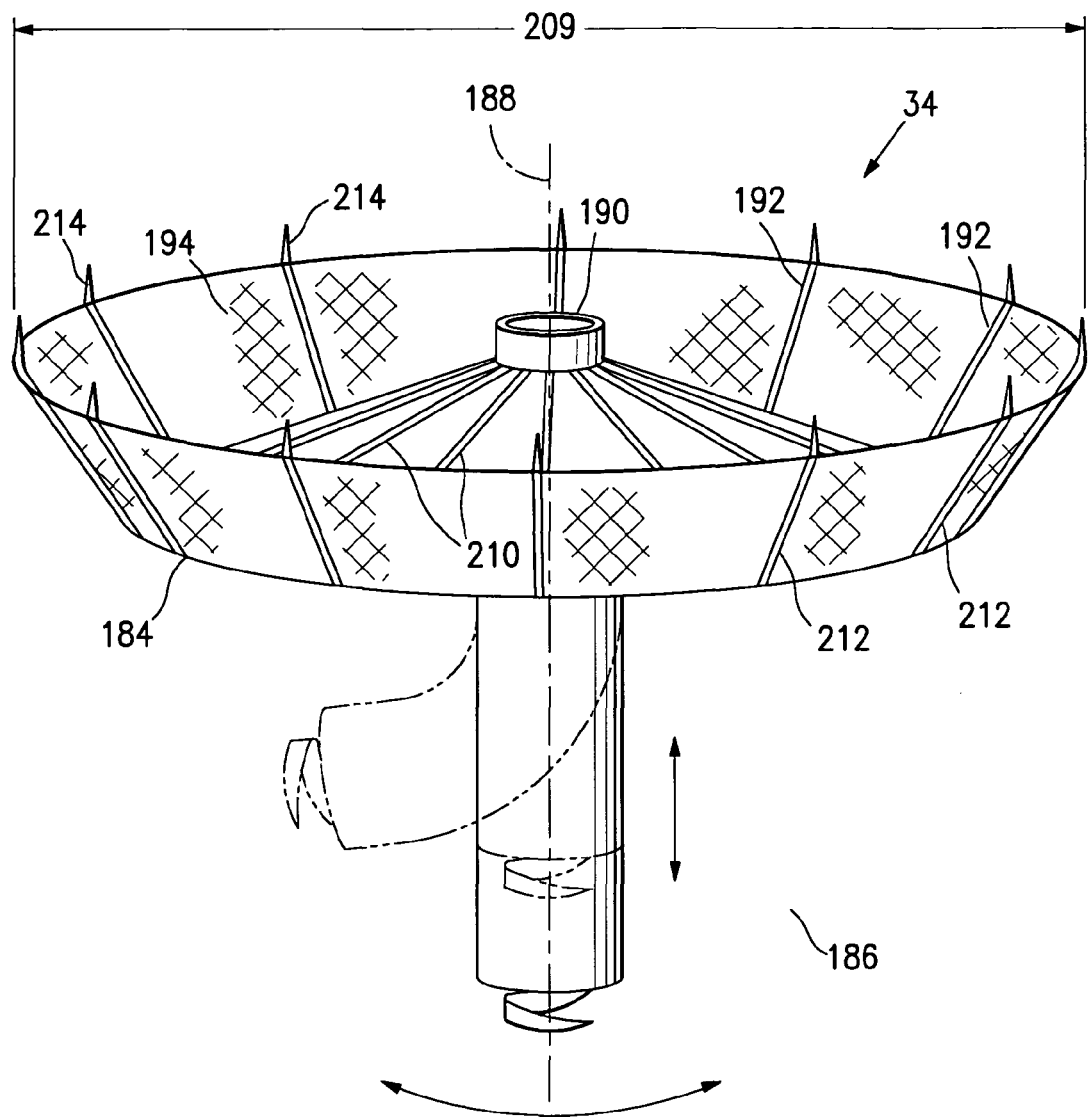
FIG. 4 is a perspective view of the cardiac device including a hub, a frame, and a stem thereof.
Figure 5A:
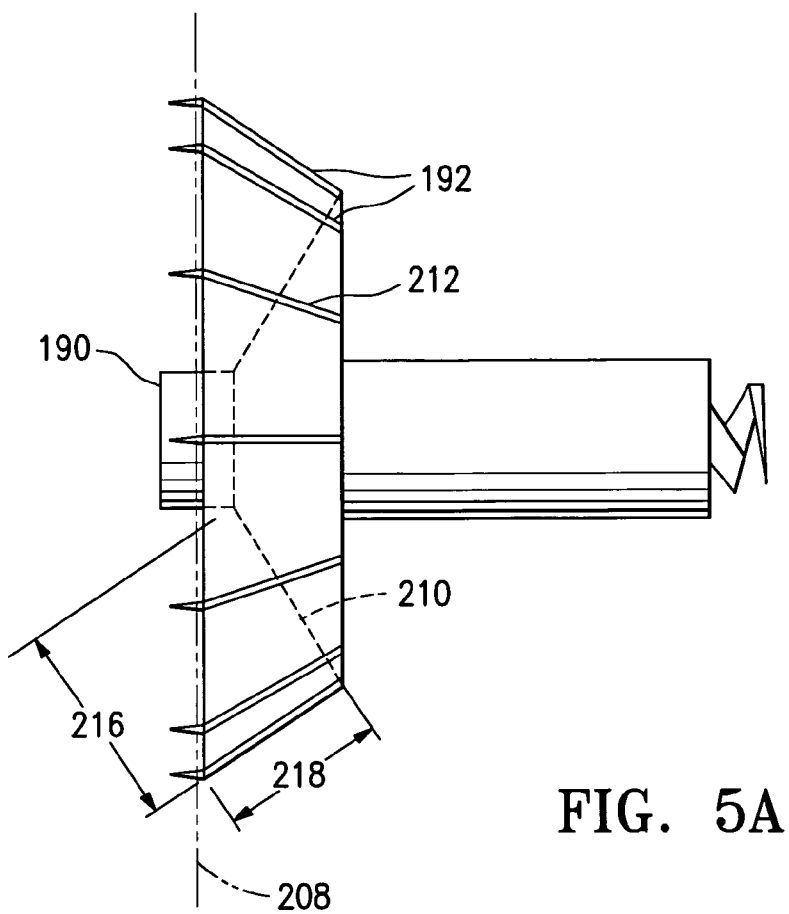
FIG. 5A is a side view of the cardiac device.
Figure 5B:
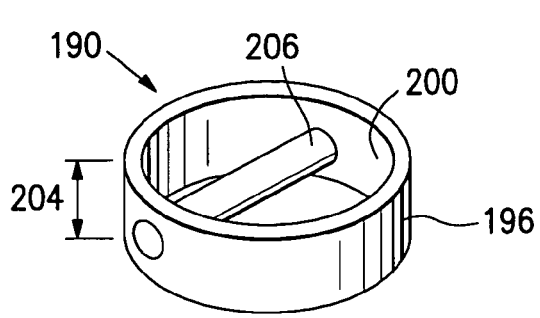
FIG. 5B is a perspective view of the hub.
Figure 5C:
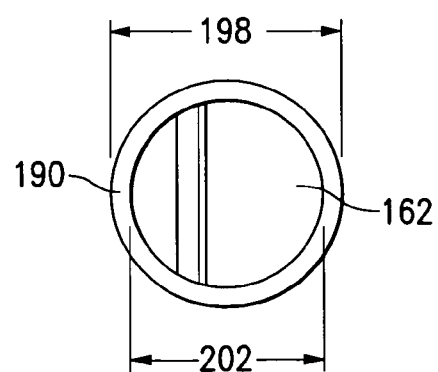
FIG. 5C is a top plan view of the hub.

FIGS. 2, 3A, 3B, and 3C illustrate the deployment mechanism 36 in more detail. FIG. 2 illustrates the handle 44 while FIGS. 3A, 3B, and 3C illustrate components at the distal end 54 of the deployment member 46. The components of the deployment mechanism 36 are primarily circular with center lines on a common axis.

The handle 44 is made of molded plastic and includes a main body 56, an anchor knob 58, an end piece 60, a proximal rotating hemostatic valve 62, a fluid line 64, a distal rotating hemostatic valve 66, and a detachment knob 68. The main body 56 is cylindrical with a length 70 of 80 mm and a diameter 72 of 25 mm. The main body 56 has a proximal 74 and a distal 76 opening at the respective ends thereof and a passageway 78 therethrough connecting the openings with an inner diameter 80 of 4 mm.

The proximal rotating hemostatic valve 62 is a cylindrical body with a passageway 82 therethrough having an inner diameter 84 of 4 mm, a locking hypo tube 86 within the passageway, a tapered outer end 88, and a raised formation 90 at a central portion thereof. The proximal rotating hemostatic valve 62 is rotationally secured to the proximal opening 74 of the handle 44. The locking hypo tube 86 is a cylindrical body secured within the passageway 82 of the proximal rotating hemostatic valve 62.

The end piece 60 is a cylindrical body with a passageway 92 therethrough connecting a proximal 94 and distal 96 opening at respective ends and having an inner diameter 98 of 5 mm. Raised formations 100 stand proud from respective central and outer portions of the end piece. A cylindrical end piece pin 102 is connected to an inner surface and extends across the inner diameter 98 of the passageway 92. The end piece pin 102 is made of stainless steel and has a length of 5 mm and a diameter of 2 mm. The distal opening 96 of the end piece 60 mates with the tapered outer end 88 of the proximal rotating hemostatic valve 62.

The anchor knob 58 is a cap-shaped body with a length 104 of 20 mm and an outer diameter 106 of 10 mm. The anchor knob 58 has a small opening 108 at a proximal end 110 with a diameter 112 of 4 mm and a large opening 114 at a distal end 116 with a diameter 118 of 6 mm. The anchor knob 58 fits over and is secured to both the end piece 60 and the proximal rotating hemostatic valve 62.

The fluid line 64 enters the handle 44 through the small opening 108 of the anchor knob 58 and is secured to the proximal opening 94 of the end piece 60. The fluid line 64 has an outer diameter 120 of 5 mm.

The distal rotating hemostatic valve 66 is a cylindrical body with a passageway 122 therethrough having a proximal inner diameter 124 of 4 mm at a proximal end 126 thereof and a distal inner diameter 128 of 5 mm at a distal end 130 thereof. The distal end 130 is tapered, and a raised formation 132 lies at a central portion thereof. The distal rotating hemostatic valve 66 is rotationally secured to the distal opening 76 of the main body 56.

The detachment knob 68 is a cap-shaped body with a length 134 of 20 mm and an outer diameter 136 of 20 mm. The detachment knob 68 has a large opening 138 at a proximal end 140 with a diameter 142 of 8 mm and a small opening 144 at a distal end 146 with a diameter 148 of 5 mm. The detachment knob 68 fits over and is secured to the distal rotating hemostatic valve 66.

Referring to FIGS. 3A-3C, the deployment member 46 includes an inner torque shaft 150 and an outer torque shaft 152. The inner torque shaft has a diameter 154 of 2 mm and is made of surgical stainless steel. The outer torque shaft is a hollow, cylindrical body with an inner diameter 156 of 3 mm and an outer diameter 158 of 5 mm. The outer torque shaft 152 is a polymer.

Referring again to FIG. 2, the inner torque shaft 150 passes through the detachment knob 68, through the distal rotating hemostatic valve 66, into and out of the passageway 78 of the main body 56, through the proximal rotating hemostatic valve 62, and into the end piece 60. The proximal end of the inner torque shaft 150 is wrapped around the end piece pin 102, reenters the proximal rotating hemostatic valve 62, and is attached to the locking hypo tube 86 within the proximal rotating hemostatic valve 62.

The outer torque shaft 152 is coaxial with and surrounds the inner torque shaft 150. A proximal end 160 of the outer torque shaft 152 passes into the distal hemostatic valve 66 and is secured thereto.

The distal end 54 of the deployment member 46 includes a key 162, a detachment screw 164, and a securing mechanism 166. A distal end 168 of the inner torque shaft 150 extends out of a distal end 170 of the outer torque shaft 152, and the key 162 is attached thereto. The key 162 is rectangular with a length 171 of 7 mm and a height 172 of 3 mm. The key 162 has a semi-circular cross section with a radius 174 of 1.5 mm. The detachment screw 164 is attached to the distal end 170 of the outer torque shaft 152, extends to a length 176 of 7 mm, and has a diameter 178 of 5 mm.

The securing mechanism 166 includes an inner component 180 and an outer component 182. The inner component 180 is a raised cylindrical portion coaxial with and on the inner torque shaft 150. The inner component 180 stands proud of the inner toque shaft 150 by 0.5 mm. The outer component 182 is a hollow, cylindrical body secured to an inner surface of the outer torque shaft 152 and has proximal and distal openings with diameters of 2.25 mm so that the inner toque shaft 150 cannot move axially relative to the outer torque shaft 152.

FIGS. 4, 5A-5C, and 6 illustrate the cardiac device 34 in more detail. The cardiac device 34 includes a frame 184 and a stem 186, or flexible body, and has a vertical axis 188.

The frame 184 includes a frame hub 190, a plurality of main segments 192, and a membrane 194. The hub 190 is a ring-shaped body with an outer surface 196 with a diameter 198 of 5 mm, an inner surface 200 with a diameter 202 of 4 mm, a thickness 204 of 3 mm, and a pin 206 extending off-center across the inner surface 200 creating a smaller and a larger gap. The pin 206 has a length of 3.5 mm and a diameter of 1 mm and is located in a plane 208. The frame 184 has a diameter 209 of approximately 25 mm, however, other embodiments may have diameters of between 10 mm and 100 mm. The entire hub 190 is made of nickel titanium.

The main segments 192 include first portions, or central segments, 210, second portions, or outer segments, 212, and passive anchors 214. The first portions 210 are connected to the hub 190 at a central portion of the outer surface 196 and extend radially from the hub 190 at an angle away from the plane 208 of the pin 206 to a length 216 of 8 mm. The second portions 212 of the segments 192 are connected to ends of the first portions 210 and further extend radially from the hub 190 but at an angle towards the plane 208. The second portions 212 each have a length 218 of 5 mm. The passive anchors 214 are formed at an end of each of the second portions 212. The passive anchors 214 have sharp ends that point slightly radially from the hub 190. The segments 192 are made from nickel titanium, which after a prescribed thermal process, allows for the segments 192 to hold their shape as illustrated, for example, in FIG. 4. The entire frame 184, or just portions of the frame 184, may also be made of stainless steel.

The membrane 194 is stretched over the first 210 and second 212 portions of the segments 192 to give the frame 184 a disk like shape. The membrane 194 is made of expanded Poly Tetra Fuoro Ethylene (ePTFE) and has a thickness of 0.08 mm. Other embodiments may use a mesh membrane.

Figure 6:
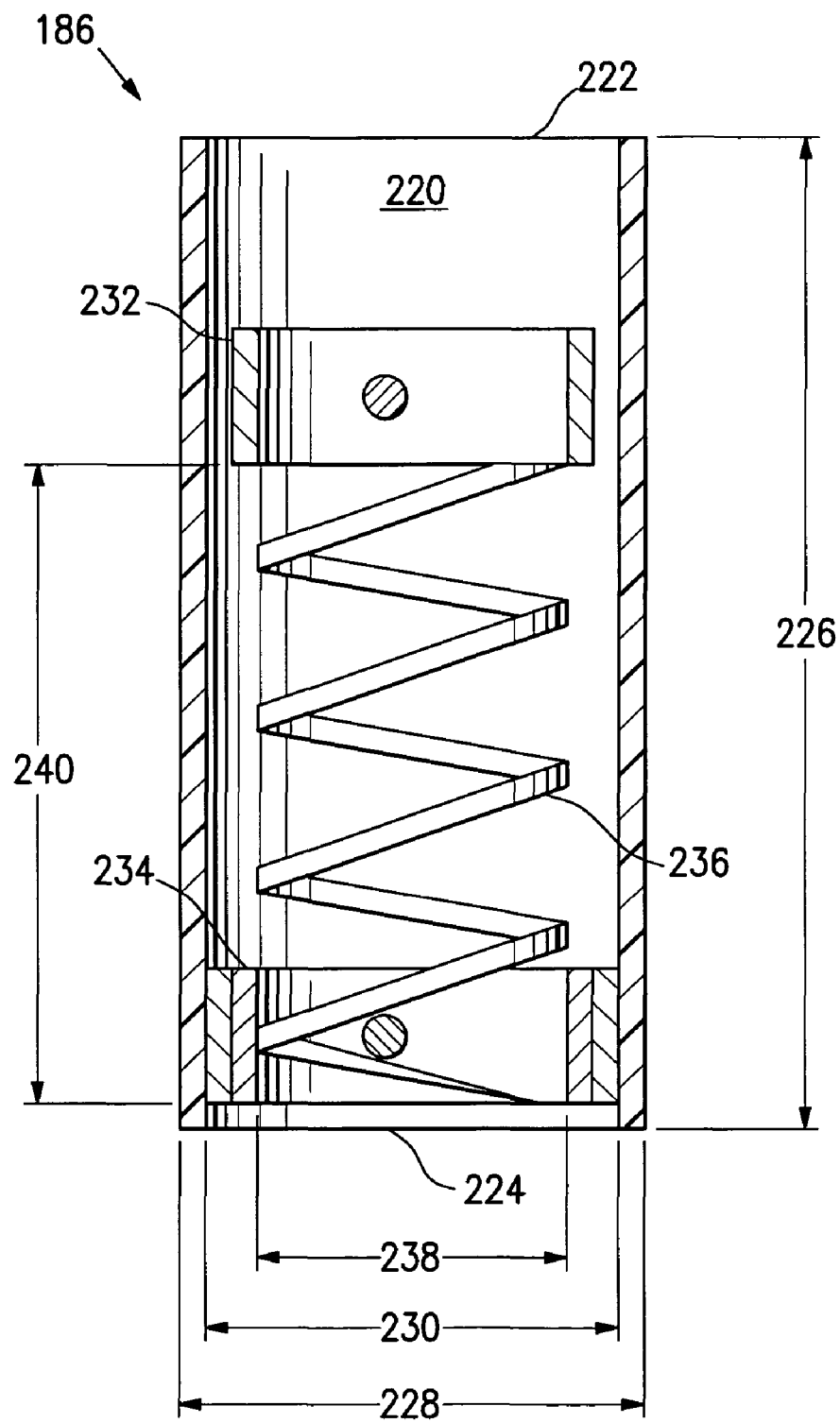
FIG. 6 is a cross-sectional side view of the stem.
Figure 7A:
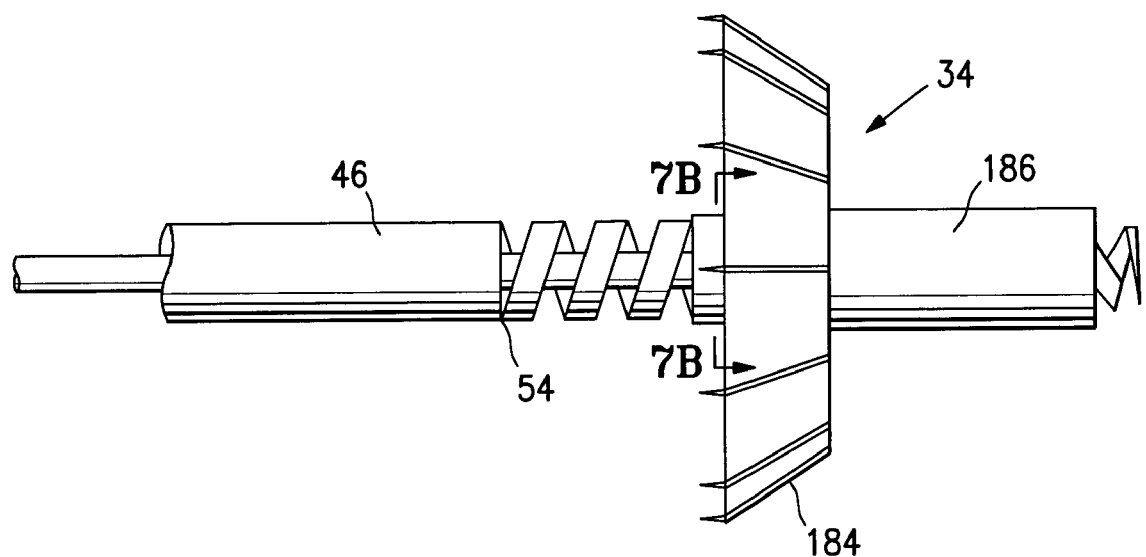
FIG. 7A is a side view of the distal end of the deployment member connected to the cardiac device.
Figure 7B:
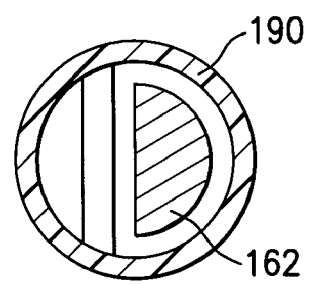
FIG. 7B is a cross-sectional view on 7B-7B in FIG. 7A of the cardiac device.

FIG. 6 illustrates the stem 186 unattached to the frame 184. The stem 186 is a hollow, cylindrical body with a passageway 220 therethough connecting a proximal 222 and a distal 224 opening. The stem 186 has a height 226 of 9 mm, an outer diameter 228 of 5 mm, and an inner diameter 230 of 4 mm. The stem 186 includes a first hub 232 and a second hub 234, both similar to the hub 190 on the frame 184. The second hub 234 is secured within the passageway 220 near the distal opening 224 of the stem 186. The first hub 232 is loose within the stem 186 so that it may move, and has an active anchor 236, in the shape of a screw, attached. The active anchor 236 spirals from the first hub 232 to engage with the pin on the second hub 234. The active anchor 236 has a diameter 238 of 3.5 mm and a length 240 of 7 mm.

The stem 186 is made of Poly Tetra Fuoro Ethylene (PTFE) and is thus expandable and flexible. Referring again to FIG. 4, the stem 186 can be compressed or stretched by 30% of its length and can be bent from the vertical axis 188 of the device 34 by 120 degrees in any direction. The first hub 232, second hub 234, and active anchor 236 are made of nickel titanium. In other embodiments, the hubs may be made of stainless steel.

FIGS. 7A, 7B, 8, and 9 illustrate the system 30 with the stem 186 connected to the cardiac device 34 and the cardiac device 34 connected to the deployment mechanism 36. The stem 186 is fused to the frame hub 190 thus securing the stem 186 to the device 34.

Figure 8:
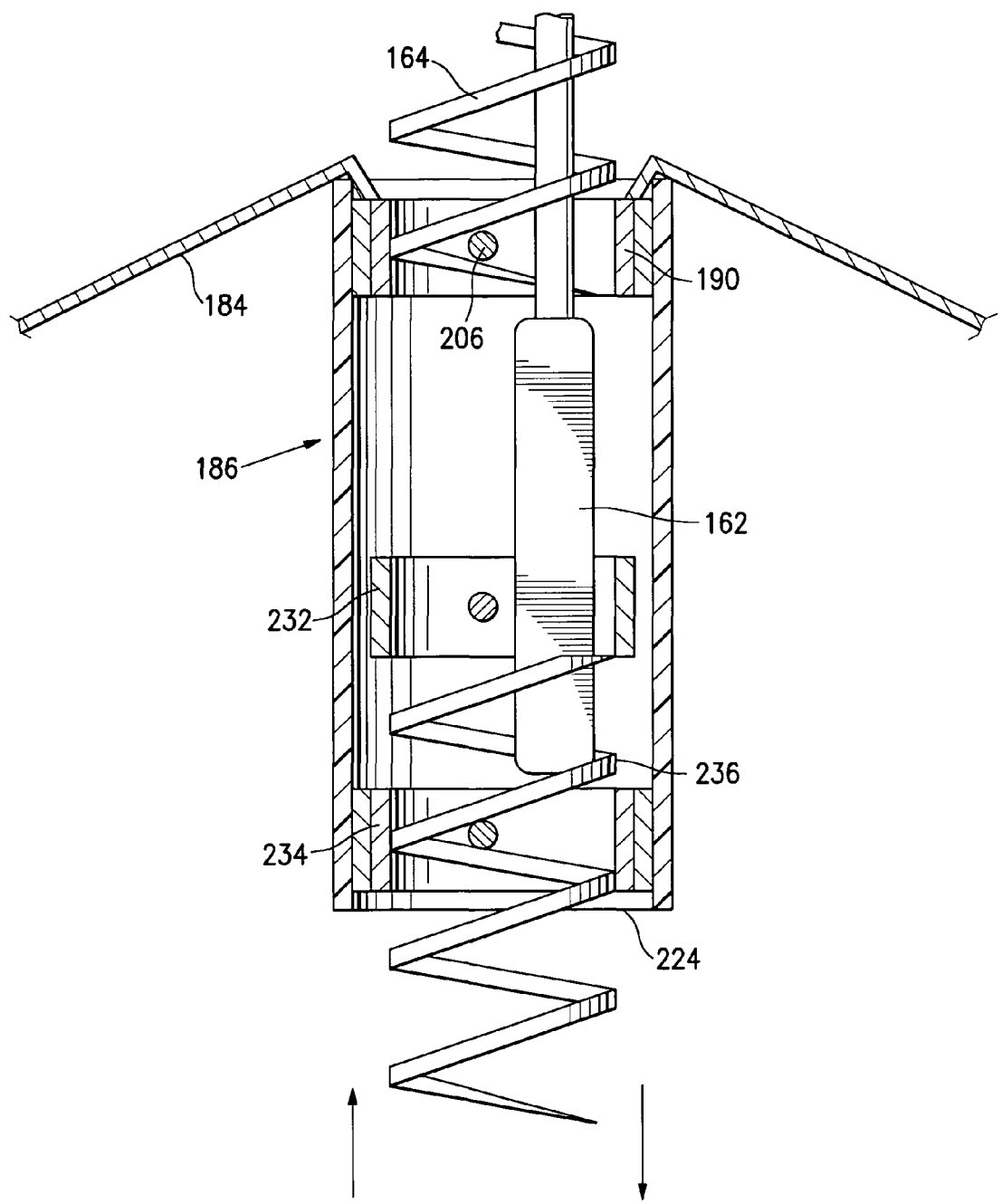
FIG. 8 is a cross-sectional side view of the cardiac device with the key connected thereto.
Figure 9:
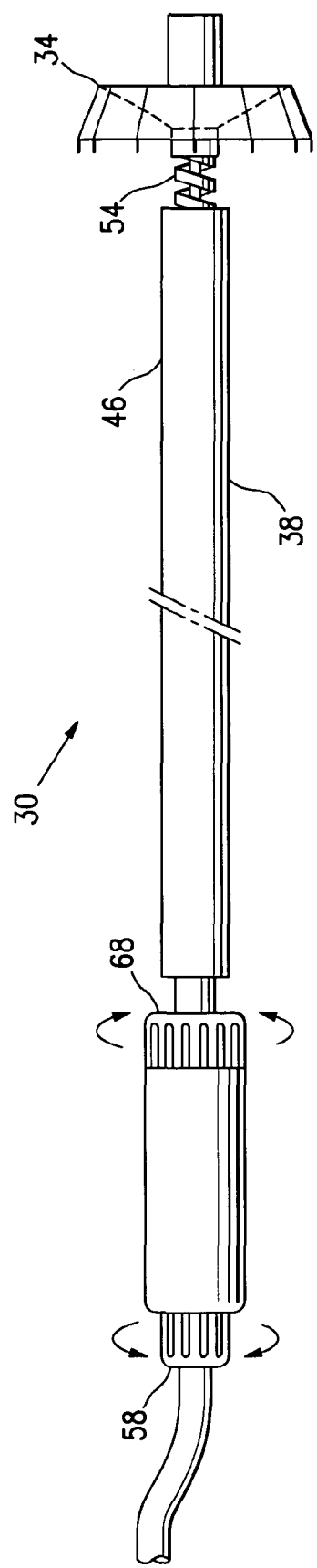
FIG. 9 is a side view of the system of FIG. 1 with the components integrated with and connected to one another.

In use, the deployment member 46 is inserted through the catheter tube 38 so that the distal end 54 of the deployment member 46 exits the distal end of the tube 38. As shown is FIGS. 7A and 7B, the deployment member 46 connects to the cardiac device 34 such that the key 162 engages the hub 190 of the frame 184 by passing through the larger gap in the hub 190. As shown in FIG. 8, the key 162 passes through the hub 190 of the frame 184 to engage with the first hub 232 of the stem 186, but does not reach the second hub 234. Once the key 162 is fully inserted into the stem 186, the detachment knob 68 is turned which rotates the outer torque shaft 152 and thus the detachment screw 164 because the detachment screw 164 is attached to the outer torque shaft 152. The rotation thereof causes the detachment screw 164 to engage with the pin 206 of the frame hub 190, securing the cardiac device 34 to the deployment mechanism 36.

Rotation of the anchor knob 58 in a first direction causes the active anchor 236 to be deployed from the distal opening 224 of the stem 186 because the anchor knob 58 is connected to the inner torque shaft 150 which, in turn, is connected to the key 162. Rotation of the key 162 causes the first hub 232 to rotate and because the active anchor 236 is connected to the first hub 232 and engaged with the pin of the second hub 234, the active anchor 236 "twists" out of the distal opening 224 of the stem while the first hub 232 is pulled toward the distal opening 224. Rotation of the anchor knob 58 in a second direction causes the active anchor 236 to reenter the distal opening 224 of the stem 186.

As illustrated in FIGS. 10A and 10B, the distal end 54 of the deployment member 46 is then pulled into the distal end of the catheter tube 38. As a proximal section of the frame 184 enters the catheter tube 38, the first portions 210 of the segments 192 begin to collapse towards the stem 186. The segments 192 collapse, or fold, against a spring force that is created by the resilient nature of the nickel titanium material from which they are made. At the same time, the second portions 212 fan out radially away from the hub 190.

As illustrated in FIGS. 11A and 11B, by the time a distal section of the frame 184 and the second portions 212 of the segments 192 begin to enter the tube 38, the second portions 212 have been bent back to collapse towards the stem 186 similarly to the first portions 210.

Figure 12A:
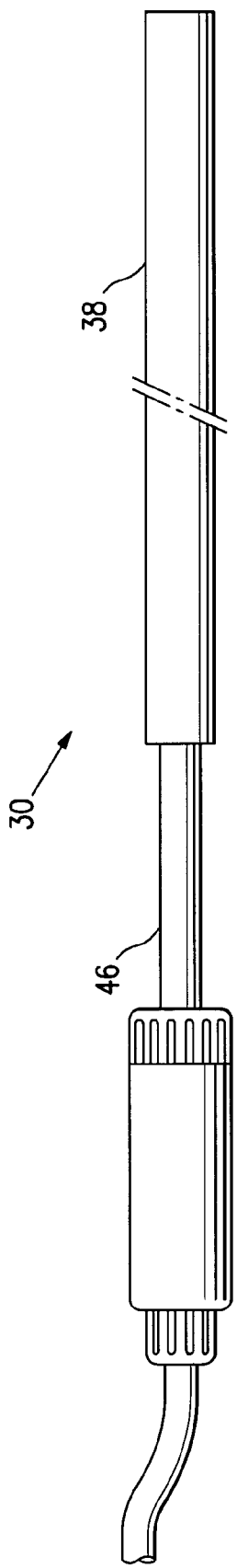
FIG. 12A is a side view of the system with the cardiac device fully retracted.
Figure 12B:
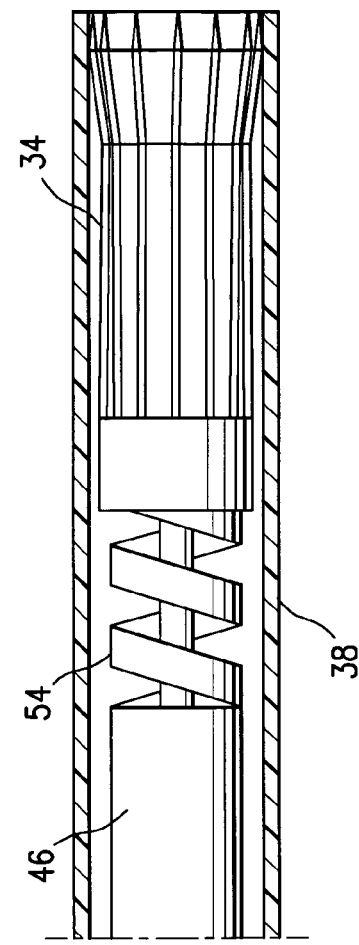
FIG. 12B is a cross-sectional side view of a portion of FIG. 12A.

FIGS. 12A and 12B illustrate the system 30 with the cardiac device 34 completely contained within the catheter tube 38.

FIGS. 13A-13J illustrate a human heart 242 while the cardiac device 34 is being deployed. The heart 242 contains a right ventricle 244 and a left ventricle 246 with papillary muscles 248 and an akinetic portion 250 with an apex 252. The distal end of the catheter 38 has been inserted through the aorta and aortic valve into the left ventricle 246 to a selected position where the cardiac device 34 can be deployed. The catheter tube 38 is then partially pulled off of the cardiac device 34 exposing the stem 186.

The active anchor 236 is then deployed by rotating the anchor knob 58 in a first direction. The active anchor 236 penetrates the myocardium of the heart 242 to secure the cardiac device 34 in the selected position at the apex 252 of the akinetic portion 250 of the left ventricle 246.

The catheter 38 is then completely removed from the distal end 54 of the deployment member 46, exposing the cardiac device 34. As the cardiac device 34 expands, due to the resilient nature of the segments 192 and the preset shape of the frame 184, the passive anchors 214 on the segments 192 penetrate the myocardium in a first direction. The membrane 194 seals a portion of the ventricle 246 and separates the ventricle 246 into two volumes, a functional portion 249 and a non-functional portion 251.

If the cardiac device 34 has not been properly positioned, or if it is of the wrong size or shape for the particular heart, the device 34 may be repositioned or completely removed from the heart 242.

Rotation of the anchor knob 58 in a second direction will cause the active anchor 236 to be removed from the apex 252 of the akinetic portion 250 of the left ventricle 246 thus releasing the cardiac device 34 from the heart 242. The distal end 54 of the deployment member 46 may be retracted into the catheter 38 to once again fold the cardiac device 34 into the position shown in FIG. 12B, from where it can again be deployed. The passive anchors 214 are removed from the myocardium in a second direction which is approximately 180 degrees from the first direction so that minimal damage is done to the myocardium.

Figure 13A:
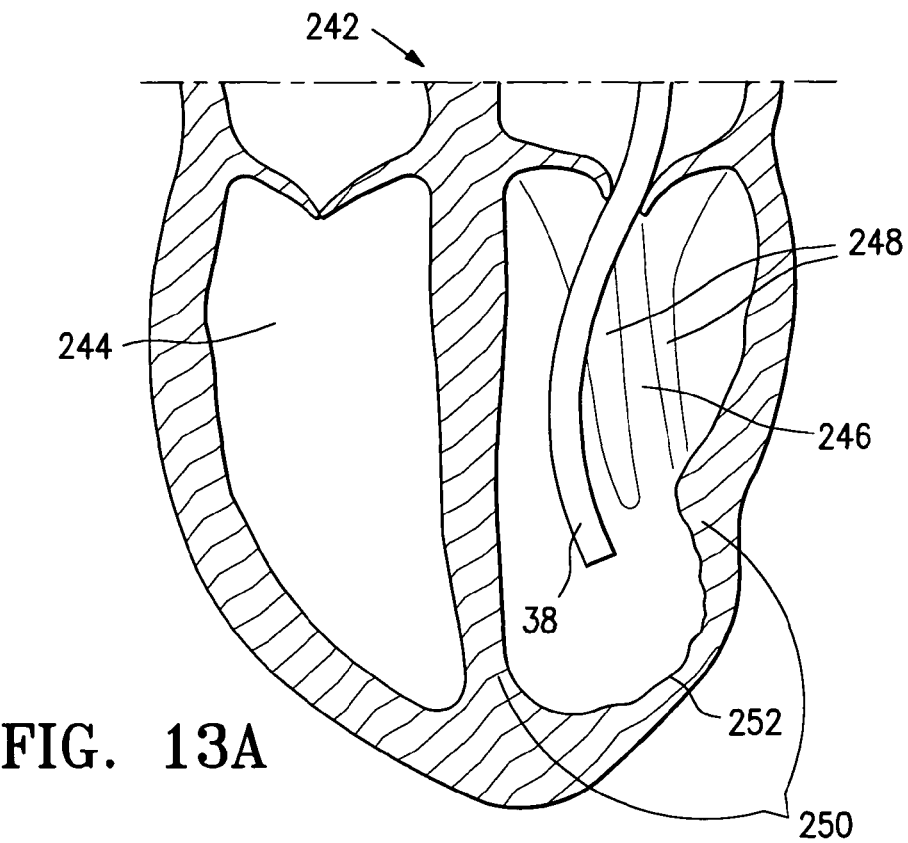
FIG. 13A is a cross-sectional side view of a human heart with the catheter inserted therein.
Figure 13B:
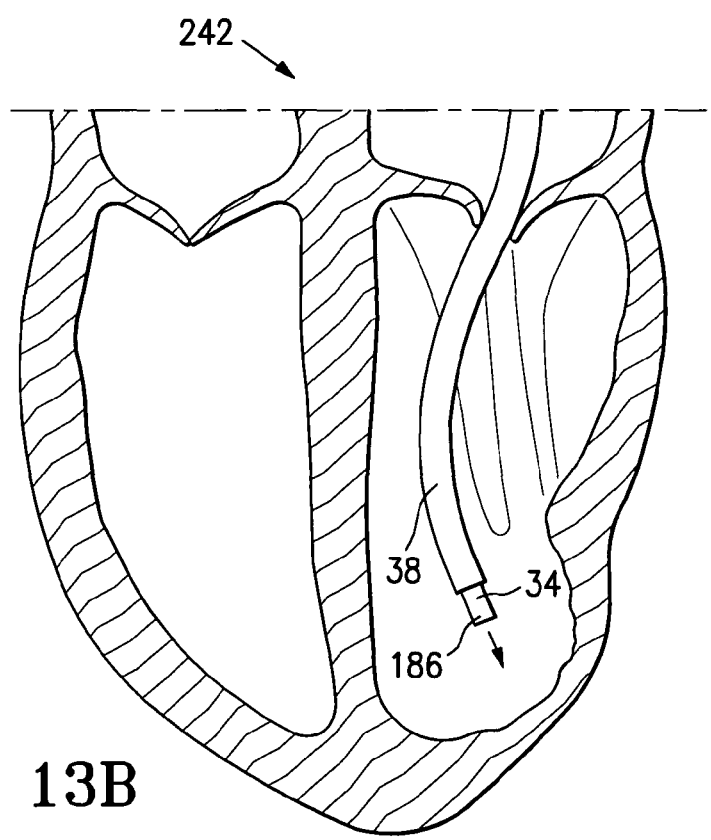
FIGS. 13B-13K are cross-sectional side views of the human heart illustrating installation (FIGS. 13B-13E), removal (FIGS. 13E-13H), and subsequent final installation (FIGS. 13I-13K) of the cardiac device.
Figure 13C:
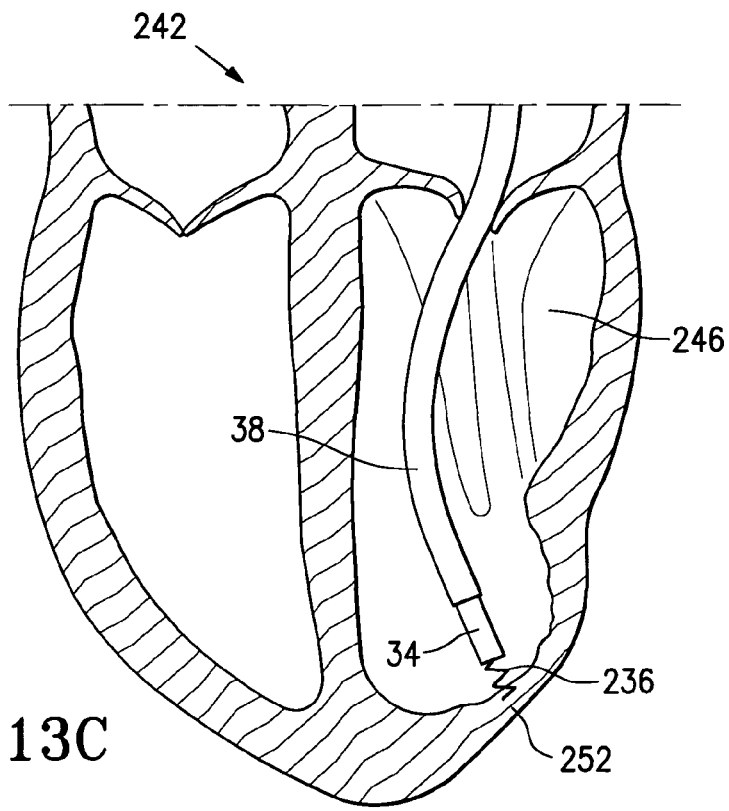
Figure 13D:
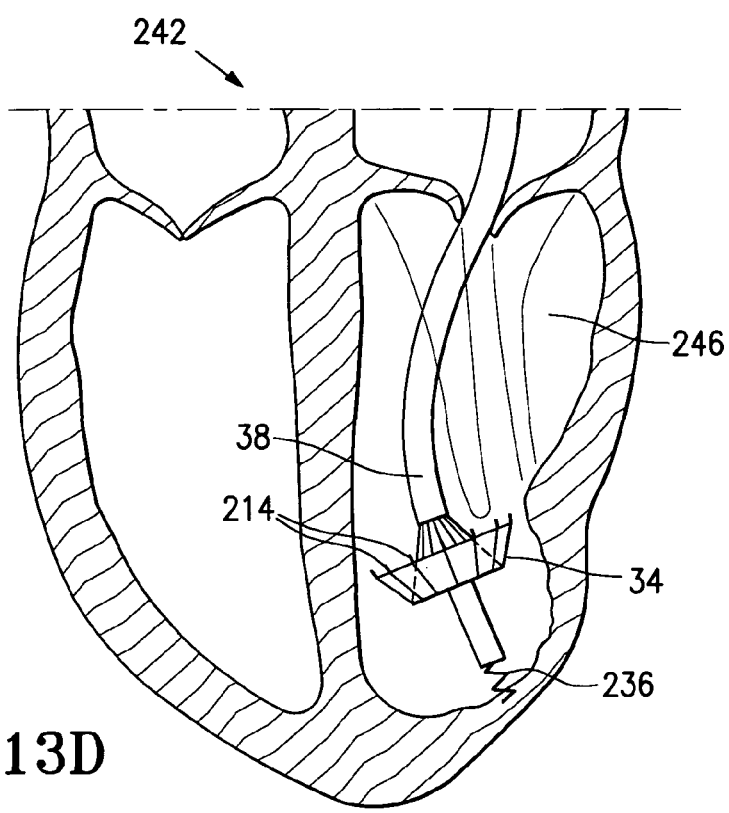
Figure 13E:
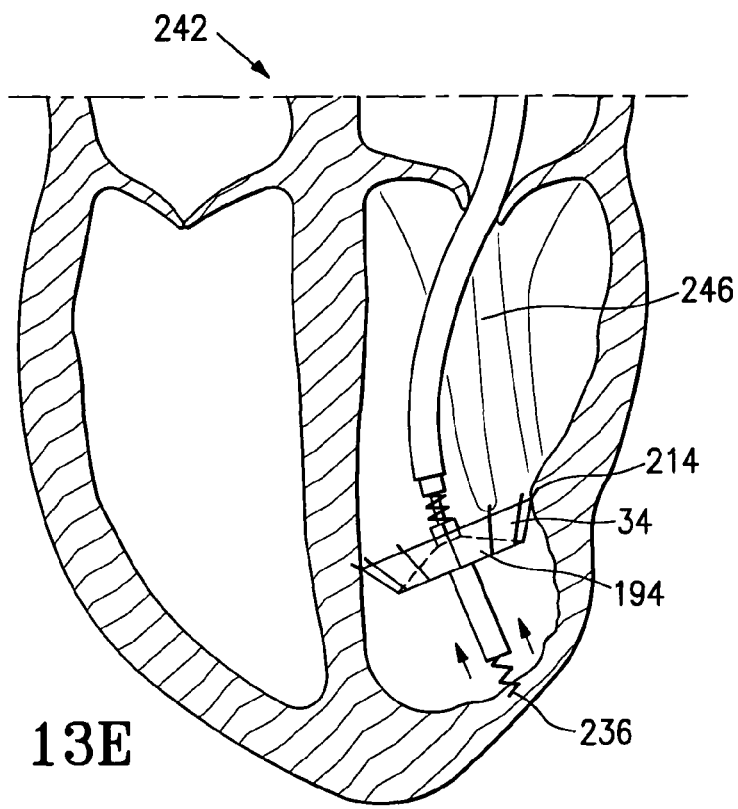
Figure 13F:
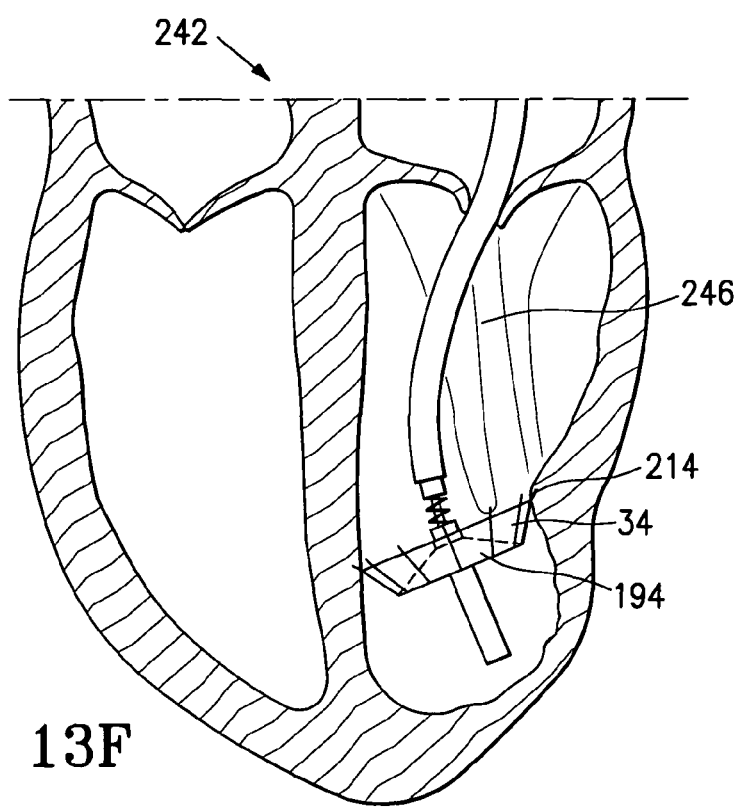
Figure 13G:
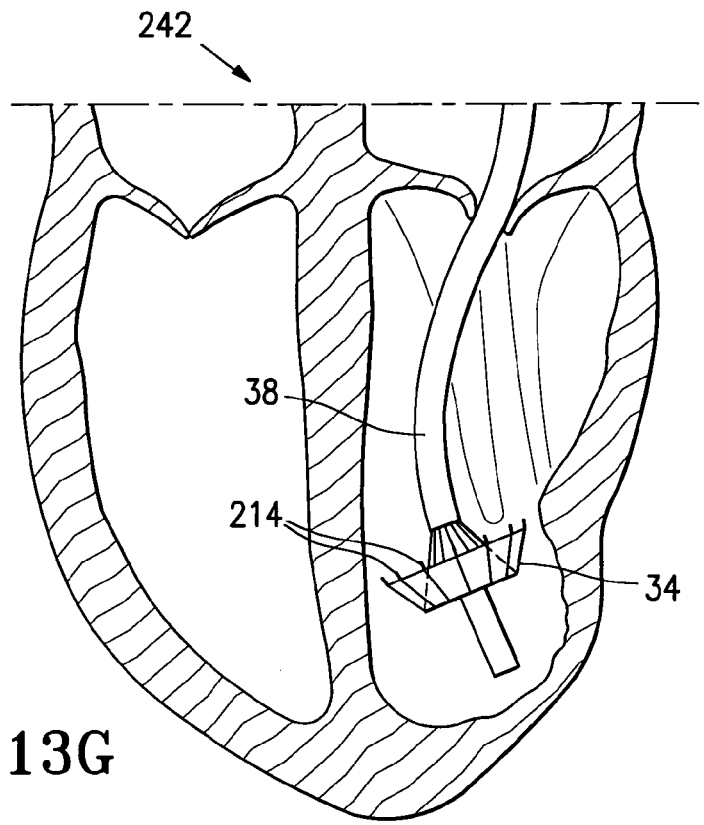
Figure 13H:
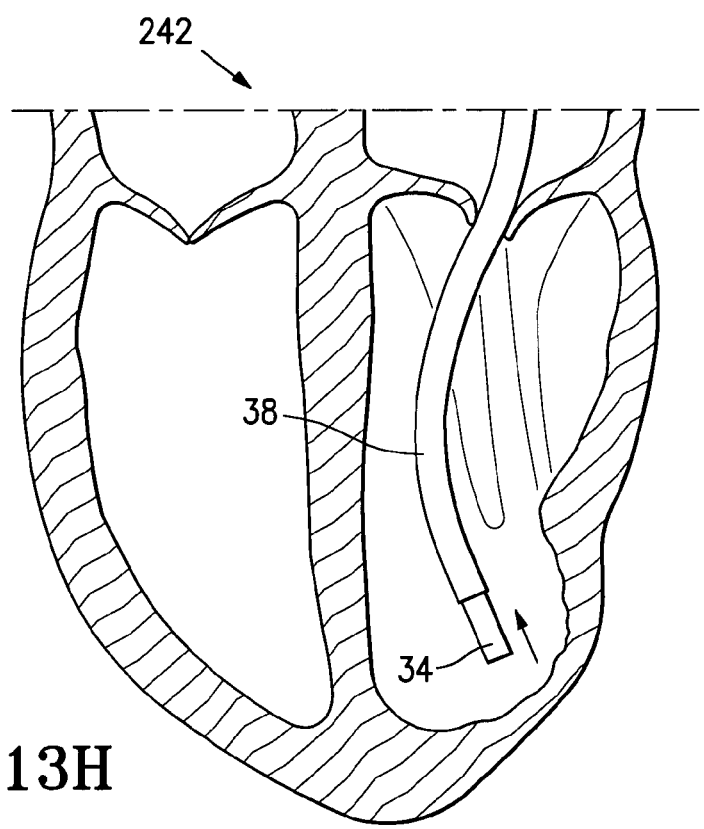
Figure 13I:
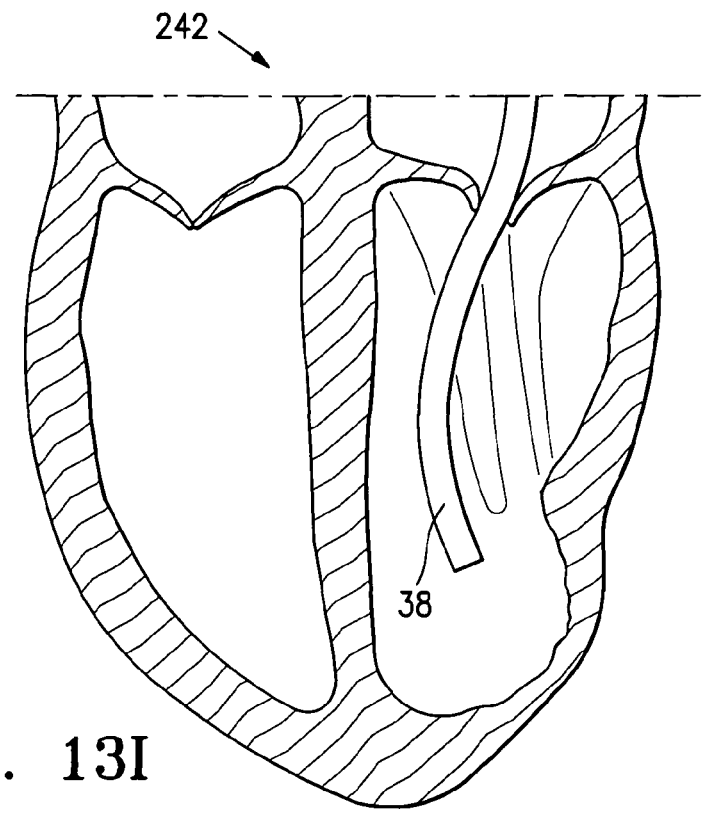
Figure 13J:
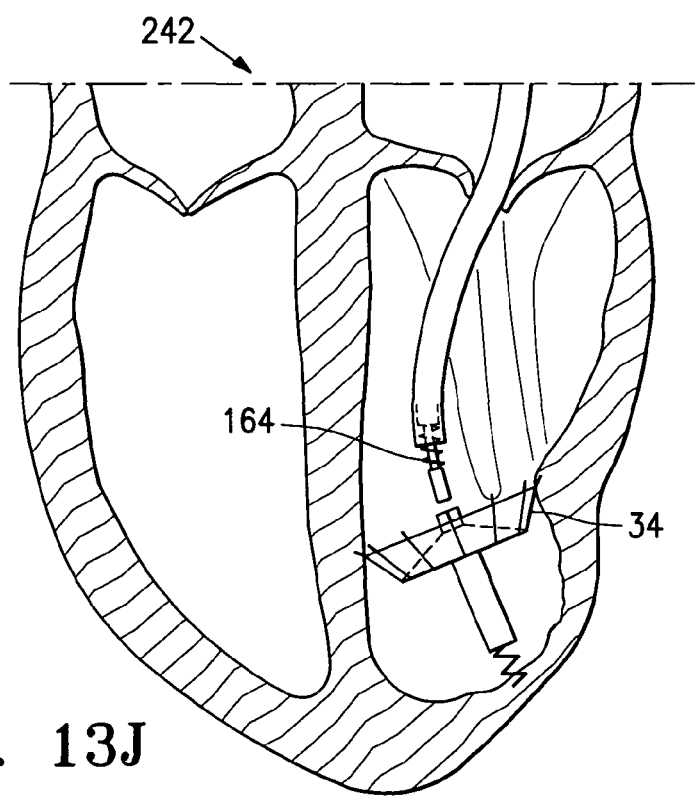
Figure 13K:
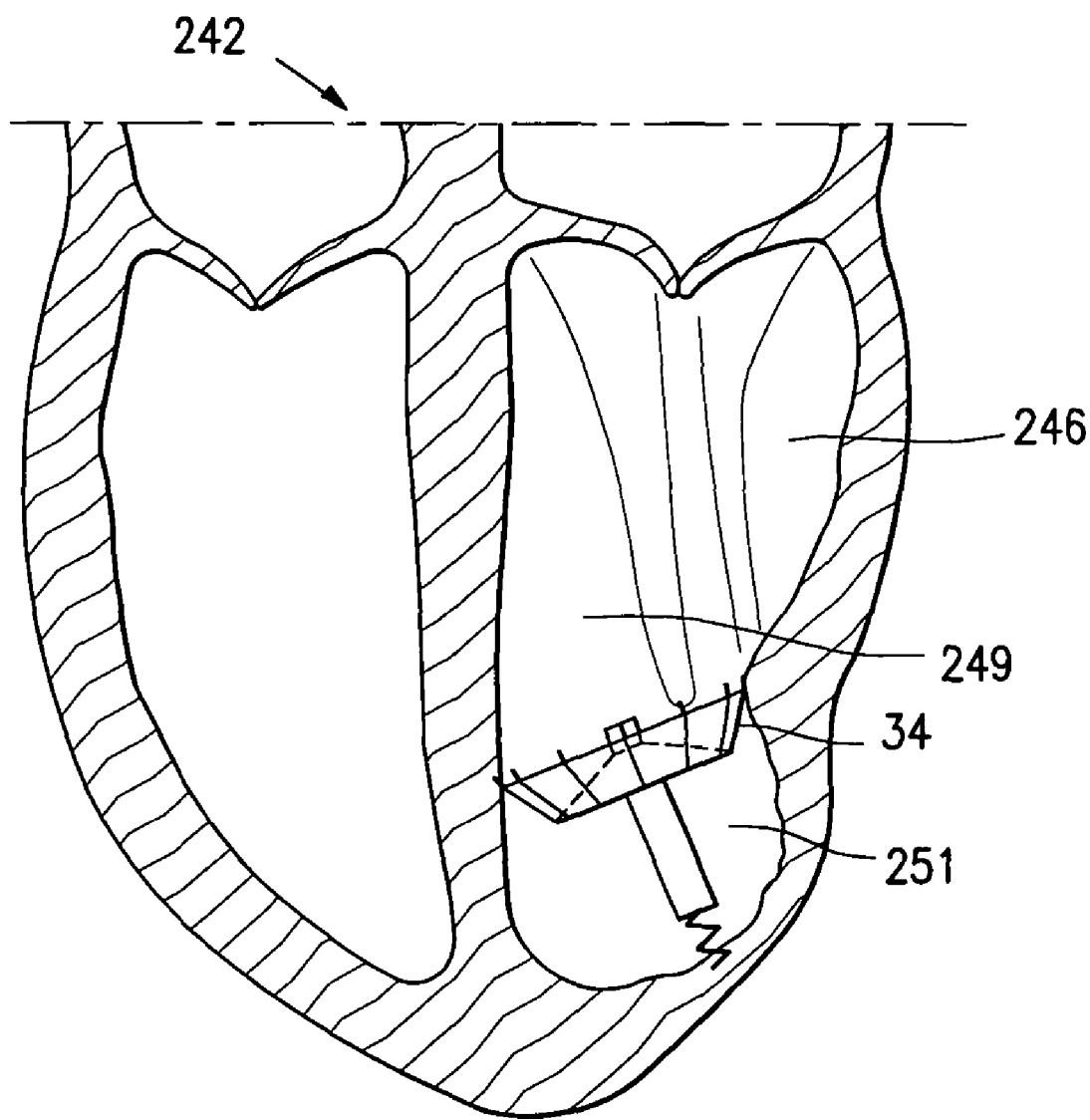

However, if the cardiac device 34 has been properly positioned and is of the proper size and shape, rotation of the detachment knob 68 in a second direction will cause the detachment screw 164 at the distal end 170 of the outer torque shaft 152 to disengage the pin 206 in the frame hub 190, thus releasing the deployment member 46 from the cardiac device 34 to allow removal of the deployment member 46 from the heart 242. FIG. 13K illustrates the heart 242 with the cardiac device 34 installed and the deployment mechanism 36 removed from the heart 242.

One advantage of this system is that the shape of the frame 184 allows the device 34 to be retrieved as long as the deployment member 46 is still connected to the device 34. When the device 34 is retrieved, the passive anchors 214 withdraw from the myocardium in a direction that is approximately 180 degrees from, or opposite, the first direction to minimize the amount of damage done to the myocardium. The device 34 also provides support for the akinetic region 250, minimizes the bulging of the akinetic region 250, and reduces stress on the working parts of the myocardium. A further advantage is that the ePTFE membrane 194 is biocompatible, has a non-thrombogenic surface, promotes healing, and accelerates endothelization.

Figure 14A:
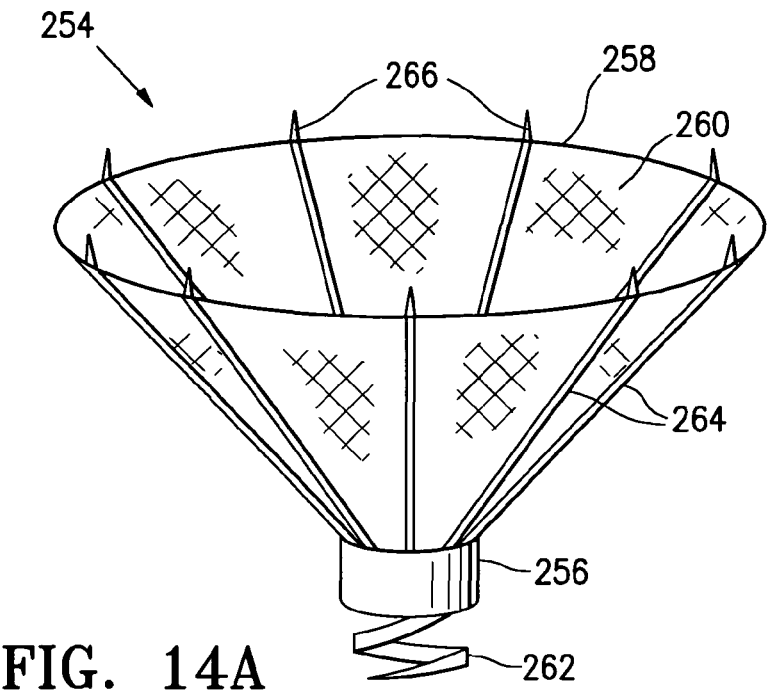
FIG. 14A is a perspective view of a cardiac device according to another embodiment of the invention.

FIG. 14A illustrates a cardiac device 254 according to another embodiment of the invention. The cardiac device includes a hub 256, a frame 258, and a membrane 260. The hub 256 lies at a central portion of the frame 258 and an active anchor 262 is connected to the hub 256 and extends downwards therefrom. The frame 258 includes a plurality of segments 264 which extend radially and upwardly from the hub 256. A sharp passive anchor 266 lies at the end of each of the segments 264. The membrane 260 is stretched between the segments 264 to form a cone-shaped body.

Figure 14B:
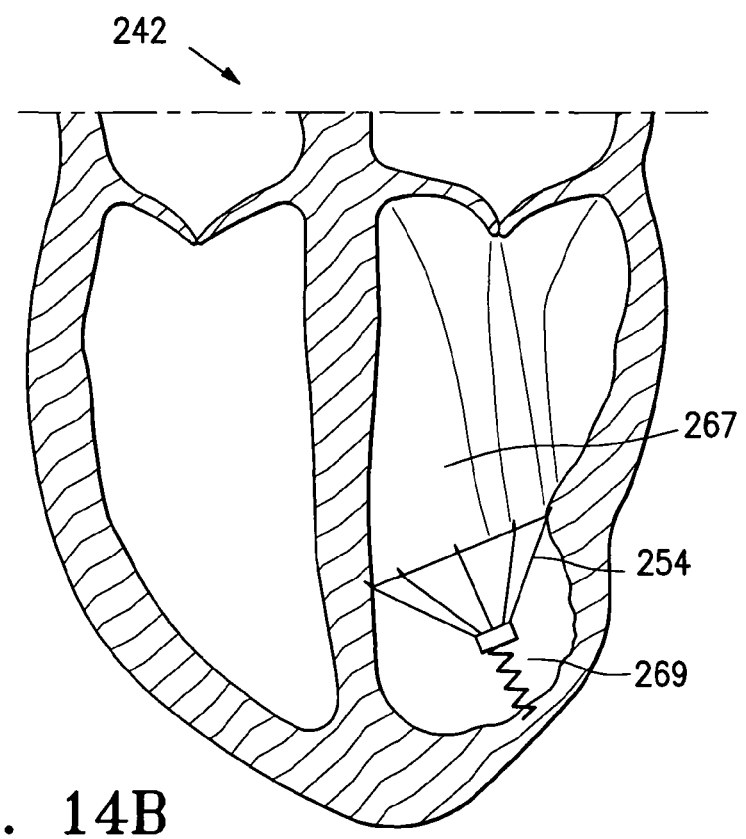
FIG. 14B is a cross-sectional side view of the human heart with the cardiac device of FIG. 14A installed.

FIG. 14B illustrates a human heart with the cardiac device 254 of FIG. 14A having been secured to an akinetic portion thereof to partition the heart chamber into to separate portions, a functional portion 267 and a non-functional portion 269.

Figure 15A:
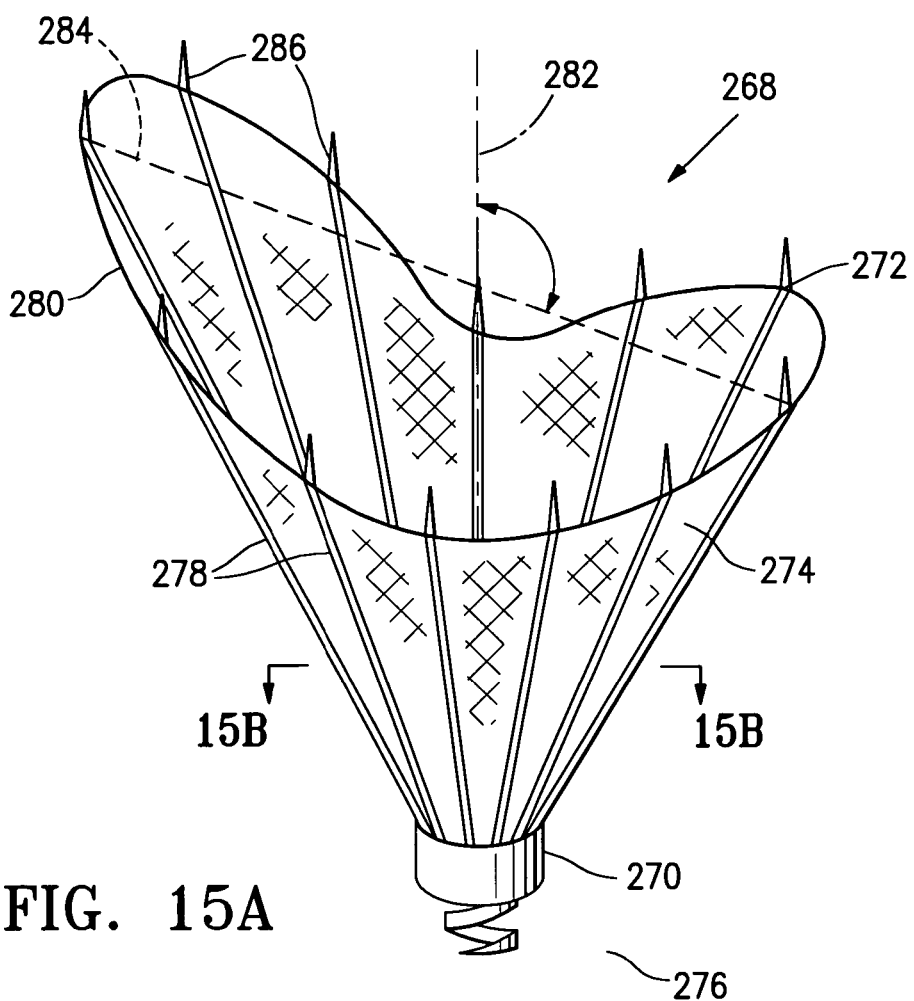
FIG. 15A is a perspective view of a cardiac device according to a further embodiment on the invention.
Figure 15B:
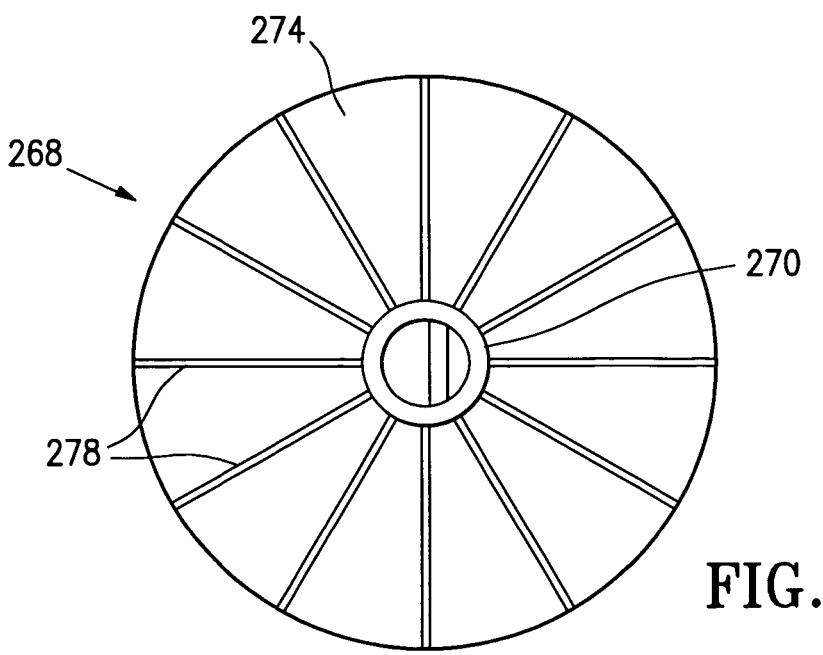
FIG. 15B is a cross-sectional top plan view of the cardiac device on 15B-15B in FIG. 15A.

FIG. 15A and FIG. 15B illustrate a cardiac device 268 according to a further embodiment of the invention. The cardiac device includes a hub 270, a frame 272, and membrane 274. The hub 270 lies at a central portion of the frame 272 and an active anchor 276 extends downwardly from the hub 270. The frame 272 includes a plurality of segments 278 which extend radially and upwardly from the hub 270. The segments 278 are of different lengths such that an outer edge 280 of the cardiac device 268 is not planar. The device 268 has a vertical axis 282 which intersects a diameter 284 across the outer edge 280 of the device 268 at an angle other than 90 degrees. A sharp passive anchor 286 lies at the end of each of the segments 278. The membrane 274 is stretched between the segments 278 to form a cone-shaped body. Referring specifically to FIG. 15B, a cross-section perpendicular to the vertical axis 282 of the device 268 is circular.

Figure 15C:
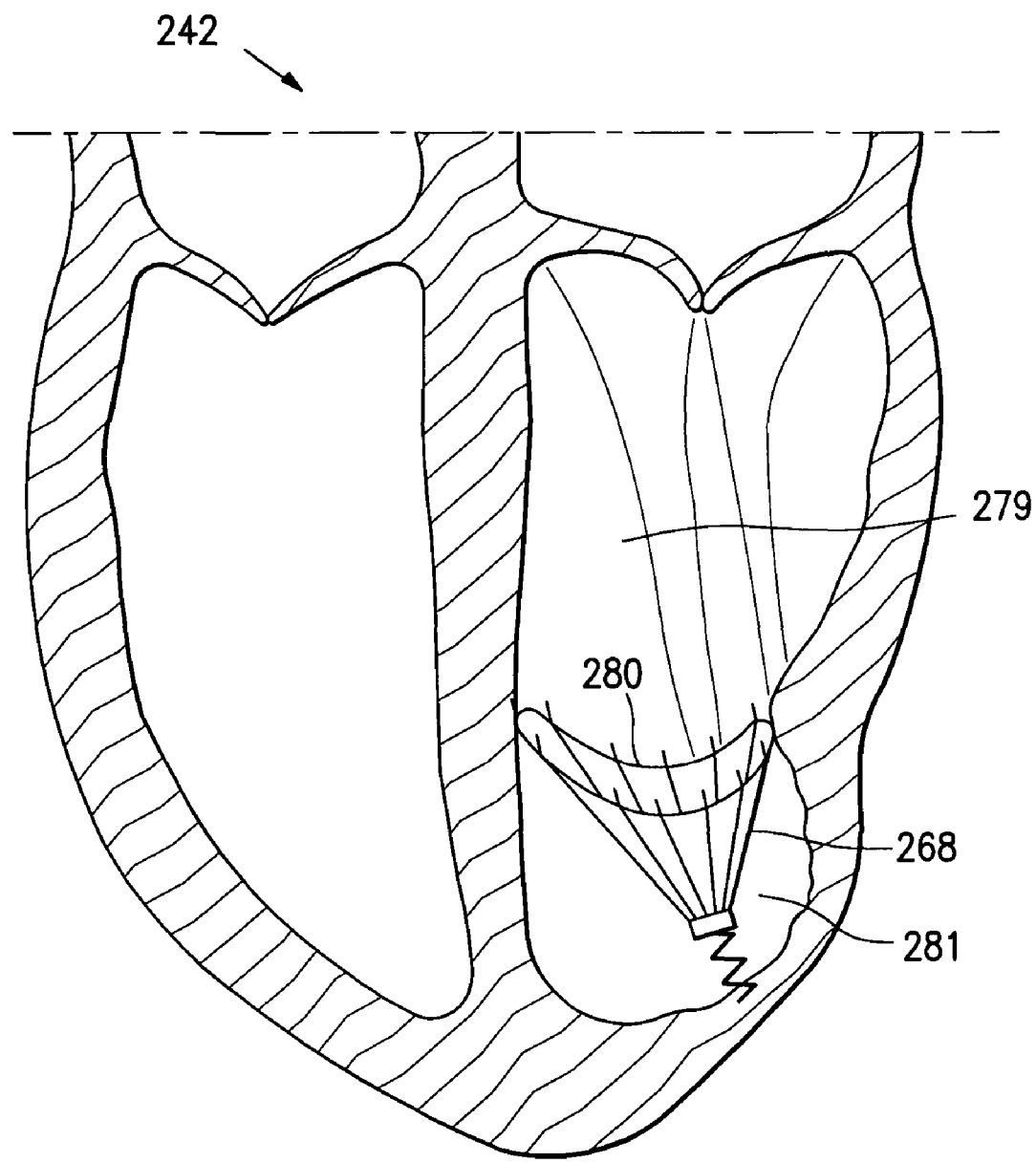
FIG. 15C is a cross-sectional side view of the human heart with the cardiac device of FIG. 15A installed.

FIG. 15C illustrates a human heart with the cardiac device 268 of FIG. 15C having been secured to an akinetic portion thereof to partition the heart chamber into a functional portion 279 and a non-functional portion 281.

A further advantage of this embodiment is that the device 268 can be sized and shaped for use on a wider variety of akinetic portions in left ventricles.

Figure 16A:
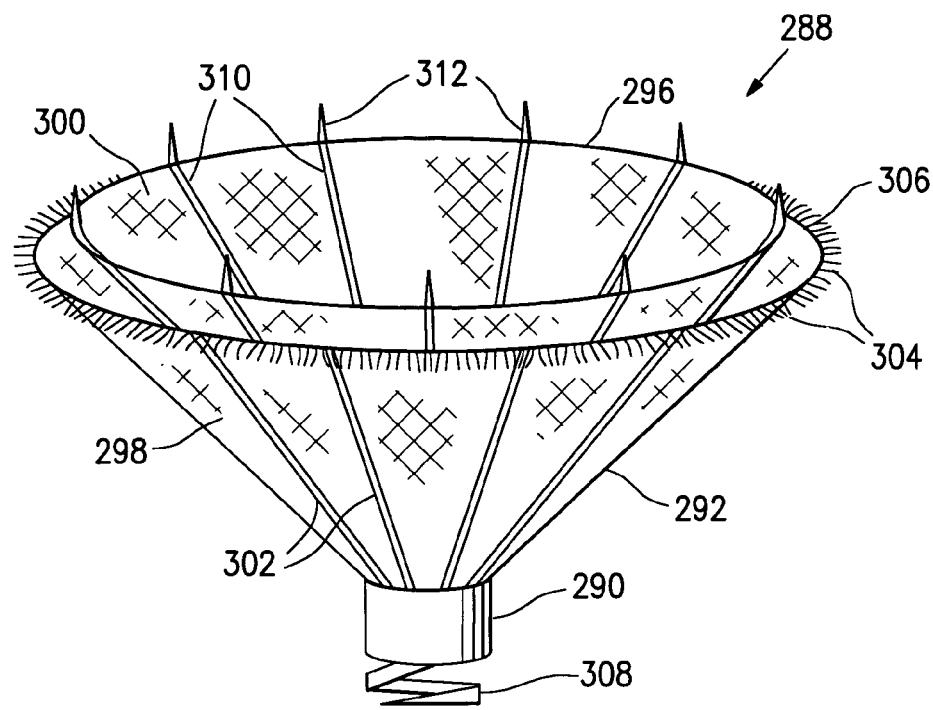
FIG. 16A is a perspective view of a cardiac device according to a further embodiment of the invention.
Figure 16B:
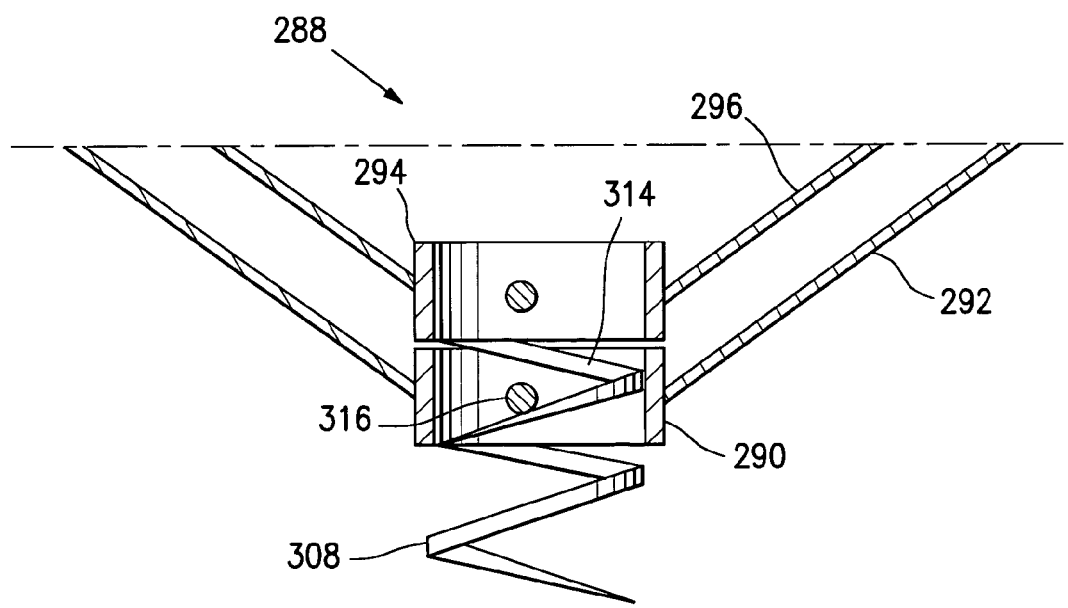
FIG. 16B is a cross-sectional side view of the cardiac device of FIG. 16A.

FIG. 16A and FIG. 16B illustrate a cardiac device 288 according to a further embodiment of the invention. The cardiac device 288 includes a first hub 290, a first frame 292, a second hub 294, a second frame 296, a first membrane 298, and a second membrane 300. The first hub 290 is attached to a central portion of the first frame 292. A plurality of segments 302 extend radially from and upwards from the first hub 290. The first membrane 298 is occlusive and made of a thrombogenic material and stretched between the segments 302 to form a first cone-shaped body. A plurality of fibers 304 extend radially from an outer edge 306 of the first cone-shaped body. An active anchor 308 extends down from the first hub 290.

The second frame 296 includes a plurality of segments 310 extending radially and upwardly from the second hub 294 and end in sharp passive anchors 312. An attachment screw 314, similar to the detachment screw 164, extends downwards from the second hub 294. Referring specifically to FIG. 16B, the attachment screw 314 is rotated so that it engages a pin 316 within the first hub 290, similarly to the frame hub 190 already described, to secure the second frame 296 to the first frame 292. The second membrane 300 is made of ePTFE and stretched between the segments 310 to form a second cone-shaped body.

Figure 16C:
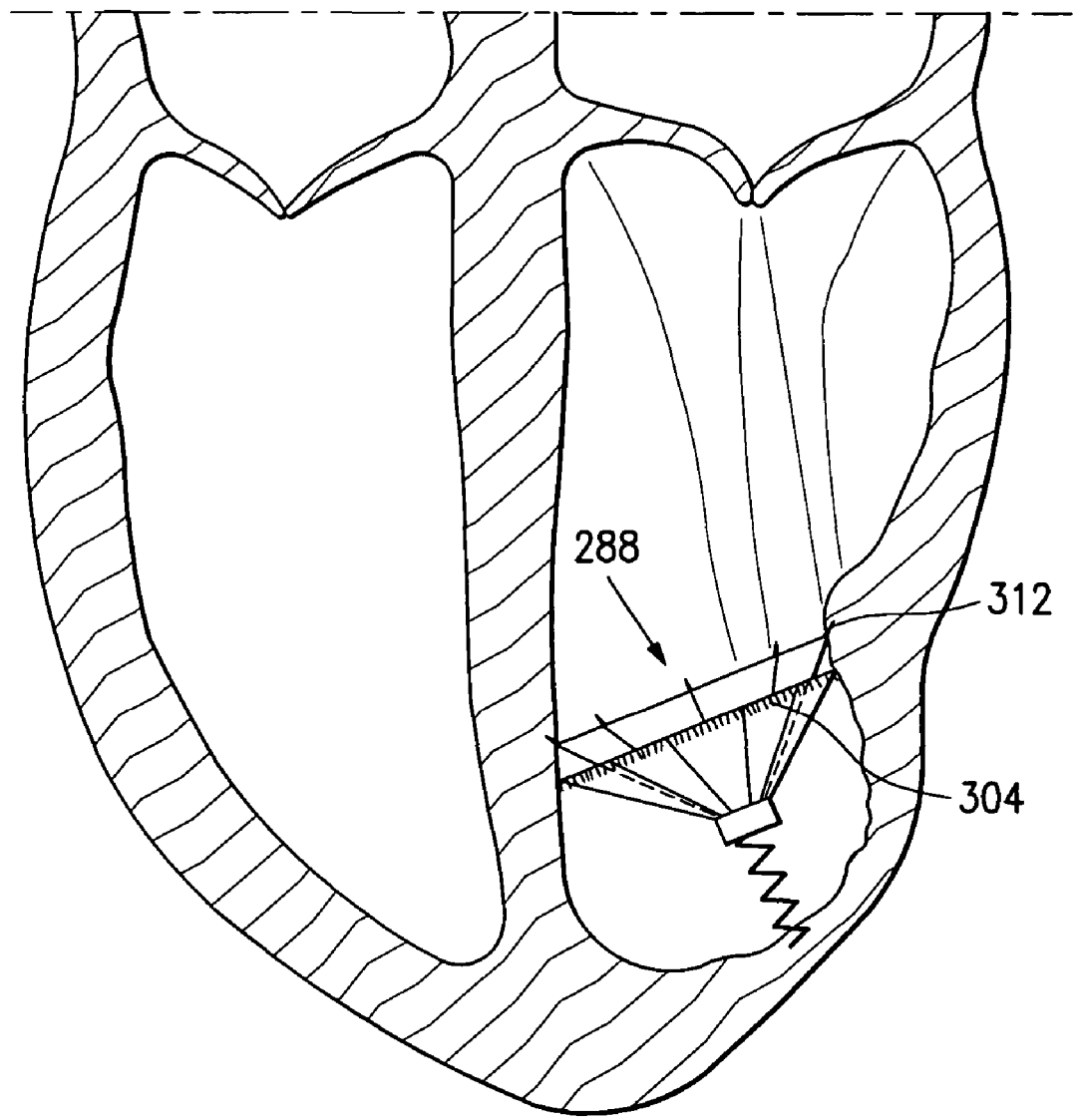
FIG. 16C is a cross-sectional side view of the human heart with the cardiac device of FIG. 16A installed.

FIG. 16C illustrates a human heart with the cardiac device 288 of FIG. 16A secured to an akinetic portion thereof. The fibers 304 on the outer edge 306 of the first frame 292 are interacting with an inner surface of the left ventricle to seal off the volume below the outer edge 306 of the first frame 292. The passive anchors 312 on the ends of the segments 310 of the second frame 296 have penetrated the myocardium to hold the device 288 in place.

A further advantage of this embodiment is that the fibers 304 of the first membrane 298 interface with trabeculae and further block the flow of blood into the apex of the akinetic portion.

Figure 17A:
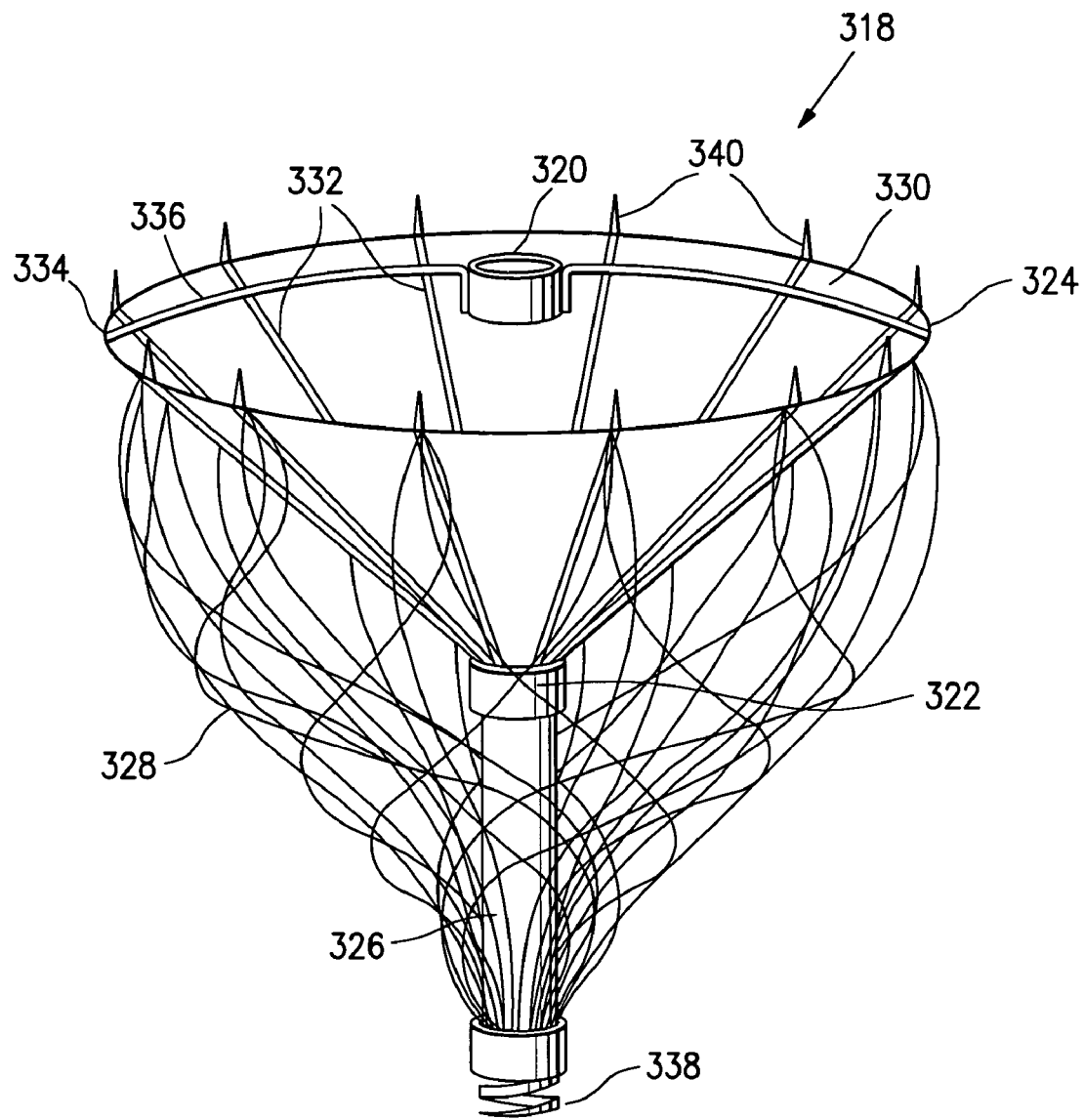
FIG. 17A is a perspective view of a cardiac device according to a further embodiment of the invention.

FIG. 17A illustrates a cardiac device 318 according to a further embodiment of the invention. The cardiac device 318 includes proximal 320 and distal 322 hubs, a frame 324, a stem 326, a braided structure 328, and a membrane 330. The frame 324 includes a plurality of segments 332 extending radially and upwards from the distal hub 322, and the membrane 330 is stretched between the segments 332 to form a cone-like body having an outer edge 334. Two extra segments 336 extend across the outer edge 334 of the cone-like body and are connected to and support the proximal hub 320 above the distal hub 322. The stem 326, including an active anchor 338, extends downwards from the distal hub 322. The braided structure 328 is made of nickel titanium and is connected to a distal end of the stem 326 into the ends of the segments 332. The segments 332 end in sharp passive anchors 340. The braided structure 328 may also be made of a biodegradable material or a polymer.

Figure 17B:
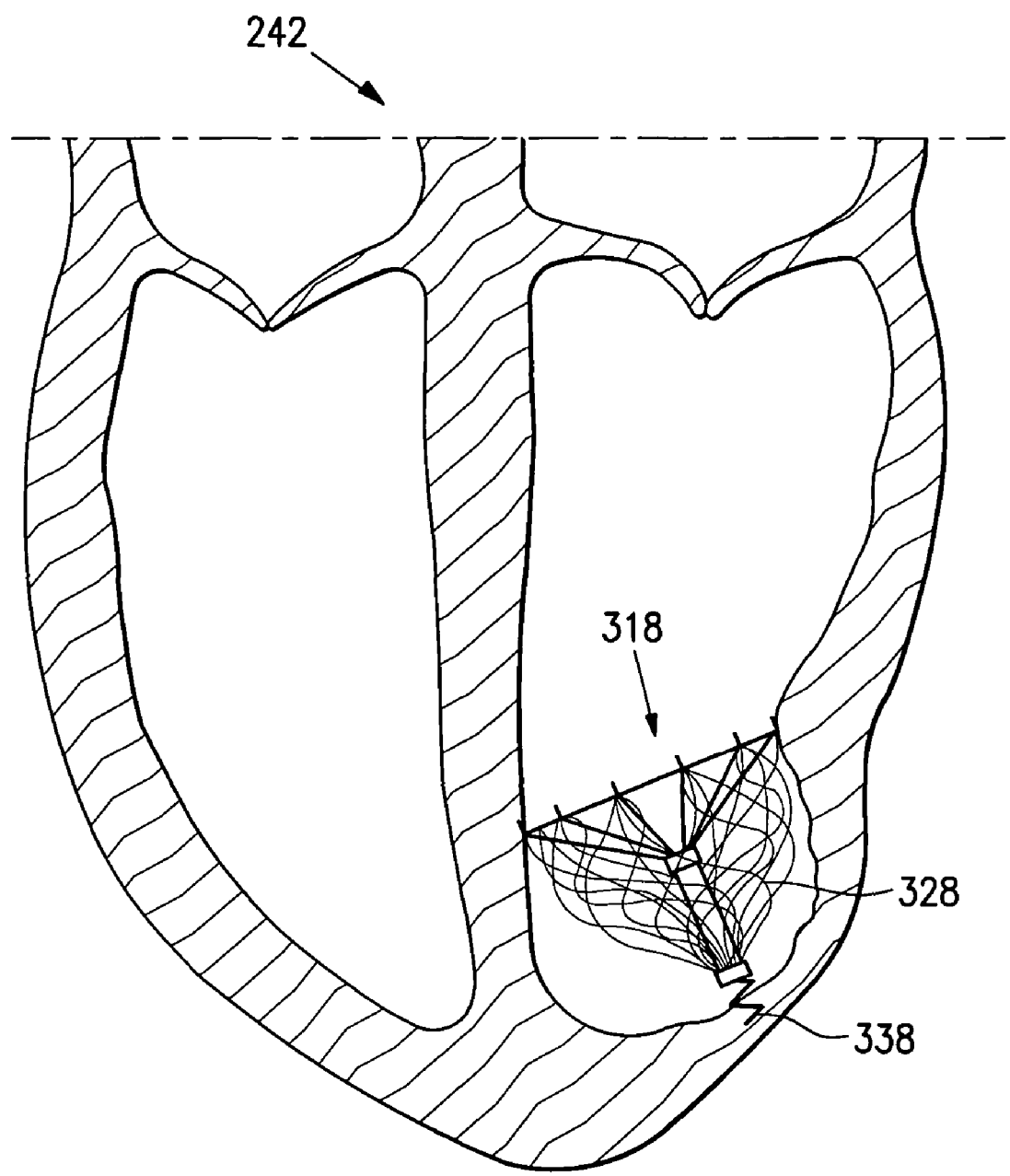
FIG. 17B is a cross-sectional side view of the human heart with the cardiac device of FIG. 17A installed.

FIG. 17B illustrates a human heart with the cardiac device 318 of FIG. 17A having been secured to an akinetic portion thereof. The braided structure 328 presses against an inner surface of the left ventricle.

A further advantage of this embodiment is that the braided structure 328 allows the device to "nestle" into position before the active anchor 338 is deployed to secure the device 318 in place. Further advantages are that the braided structure 328 adds structural stability to the device 318 and the nickel titanium of the braided structure 328 provides a mechanism for containing thrombi in the static chamber.

Figure 18A:
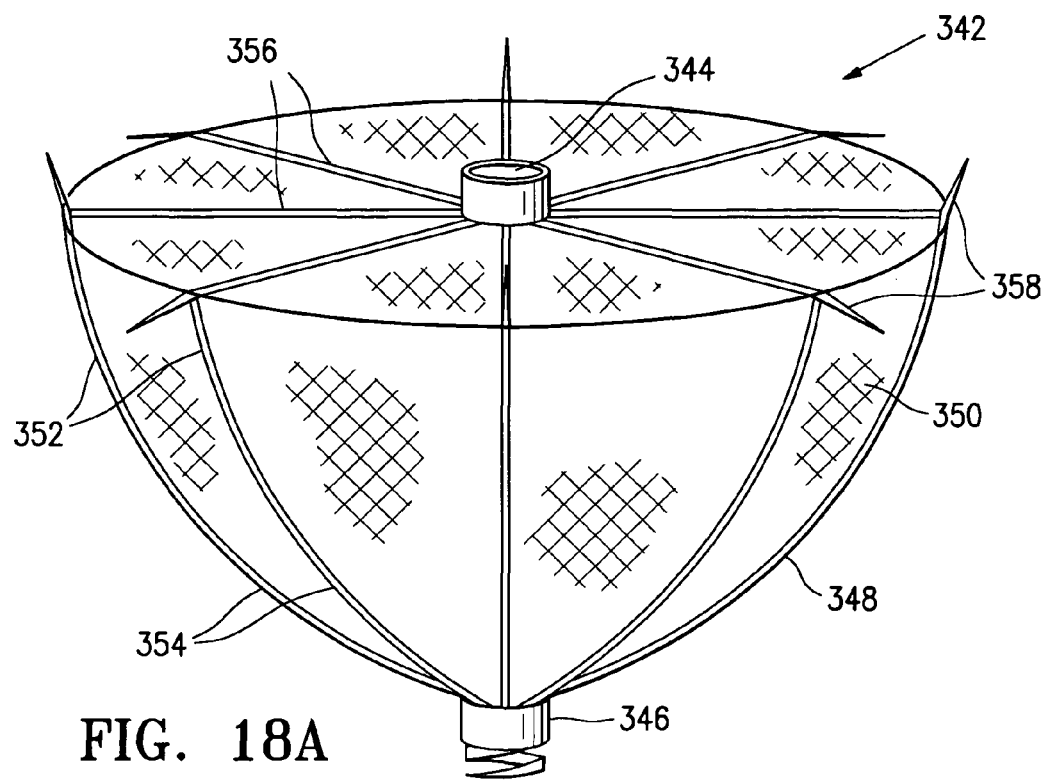
FIG. 18A is a perspective view of a cardiac device according to a further embodiment of the invention.

FIG. 18A illustrates a cardiac device 342 according to a further embodiment of the invention. The cardiac device 342 includes proximal 344 and distal 346 hubs, a frame 348, and a membrane 350. A plurality segments 352, having first 354 and second 356 portions, extend upwardly and radially from the distal hub 346 in a curved fashion and are bent and extend inwards to meet at the proximal hub 344. The membrane 350 is stretched across the segments 352 to form a semi-circular or basket-shaped body. Sharp passive anchors 358 extend from the segments 352 between the first 354 and second 356 portions.

Some of the passive anchors 358 extend in a primarily axial direction with a small radial component, and some of the passive anchors 358 extend in a primarily radial direction with a small axial component. Other embodiments may have both types of passive anchors on a single segment.

Figure 18B:
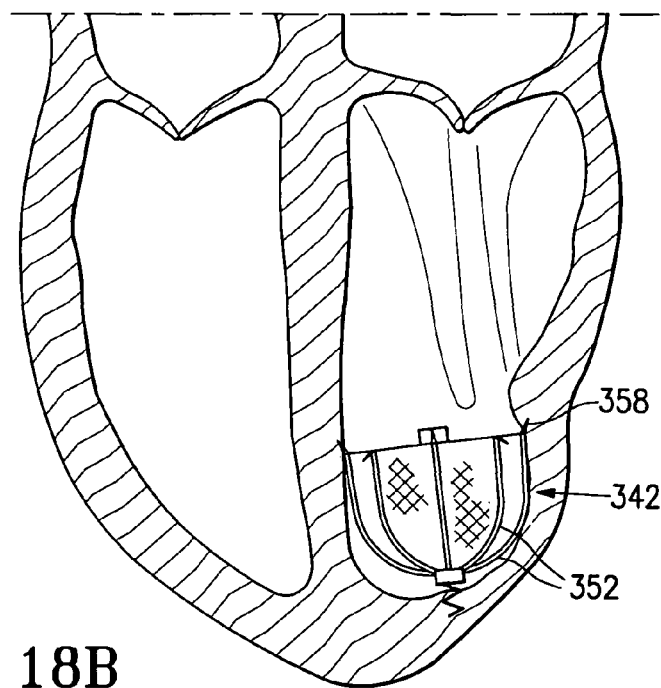
FIG. 18B is a cross-sectional side view of the human heart with the cardiac device of FIG. 18A installed.

FIG. 18B illustrates a human heart with the cardiac device 342 of FIG. 18A having been installed into an akinetic portion thereof. The segments 352 are pressed against the myocardium because the device is slightly oversized.

A further advantage of this embodiment is that because of the size of the device 342 and shape of the segments 352, the passive anchors 358 are assisted in penetrating the myocardium. A further advantage is that because of the shape of the frame 348, the device 342 can be retrieved from the left ventricle as long as the device 34 is still attached to the deployment member 46. A further advantage is that because the entire frame 348 is covered with the membrane 350, the flow of blood to the apex of the akinetic portion is even further blocked.

Figure 19A:
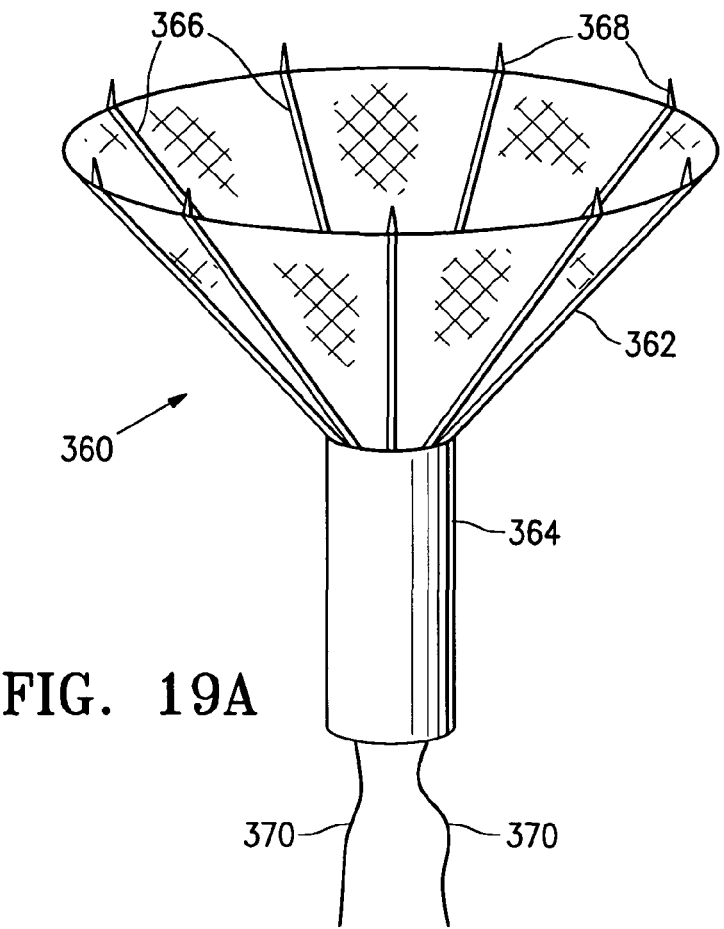
FIG. 19A is a perspective view of a cardiac device according to a further embodiment of the invention.

FIG. 19A illustrates a cardiac device 360 according to a further embodiment of the invention. The cardiac device 360 includes a frame 362 and a stem 364. The frame 362 includes a plurality of segments 366 which extend upwardly and radially from the stem 364 and end in a plurality of sharp passive anchors 368. The stem 364 extends downwards from the frame 362 and includes two suture strands 370 at a distal end thereof.

Figure 19B:
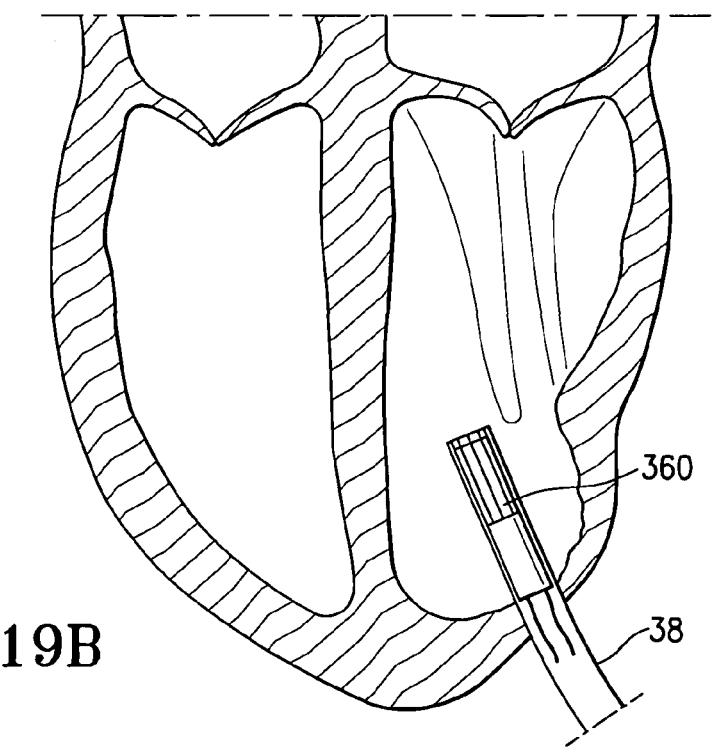
FIG. 19B is a cross-sectional side view of the human heart while the cardiac device of FIG. 19A is being installed.
Figure 19C:
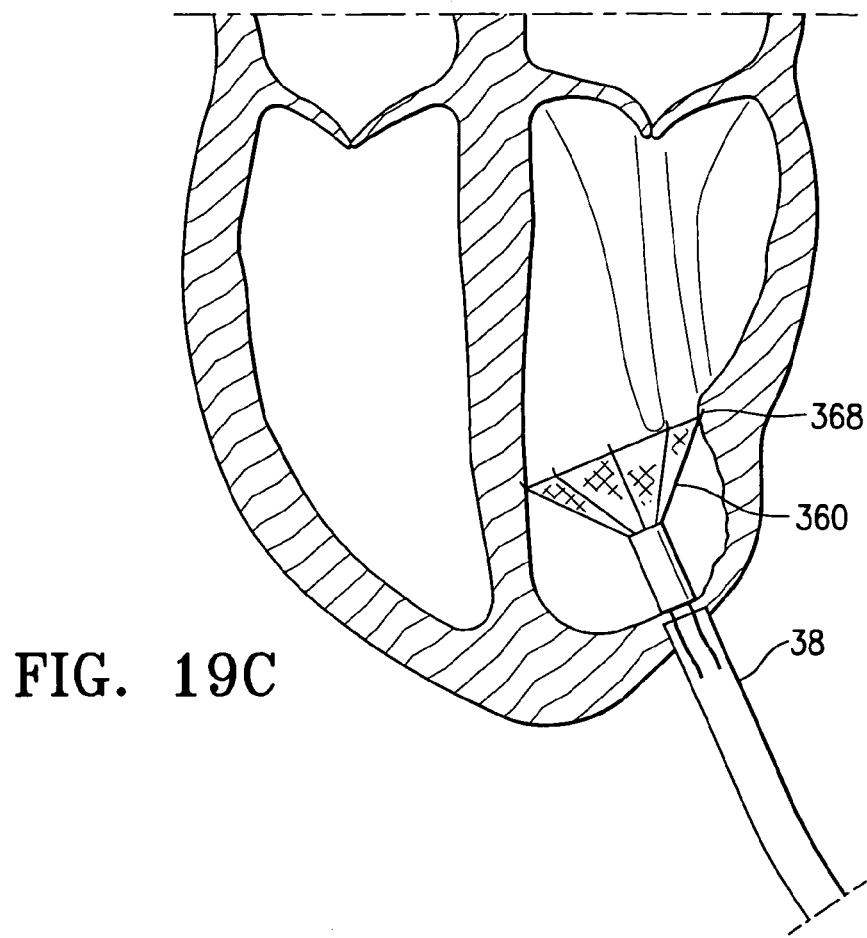
FIG. 19C is a cross-sectional side view of the human heart while the cardiac device of FIG. 19A is being installed.
Figure 19D:
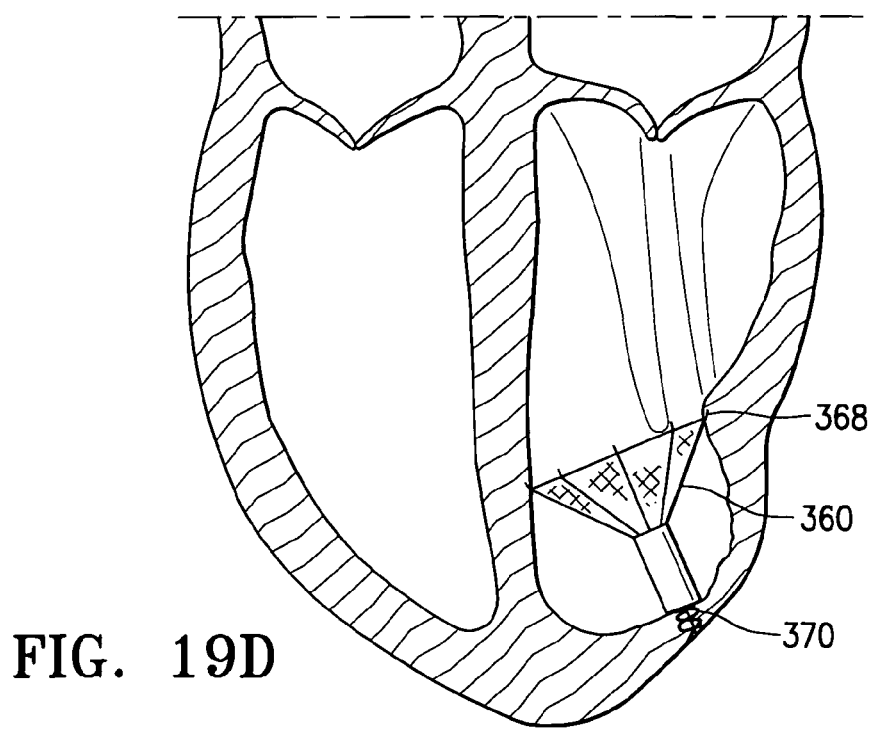
FIG. 19D is a cross-sectional side view of a human heart with the cardiac device of FIG. 19A installed.

FIGS. 19B, 19C, and 19D illustrate the installation of the cardiac device 360 of FIG. 16. While a high pressure is maintained in the left ventricle the catheter tube 38 is inserted through the outer wall into the left ventricle with the cardiac device 360 inserted in the distal end thereof. The catheter 38 is removed from the cardiac device 360, and the cardiac device 360 expands such that the passive anchors 368 are inserted into the inner surface of the left ventricle. The catheter 38 is then completely removed and the sutures 370 are used to close the insertion made by the catheter 38 and to secure the cardiac device 360 to the akinetic portion.

Figure 20A:
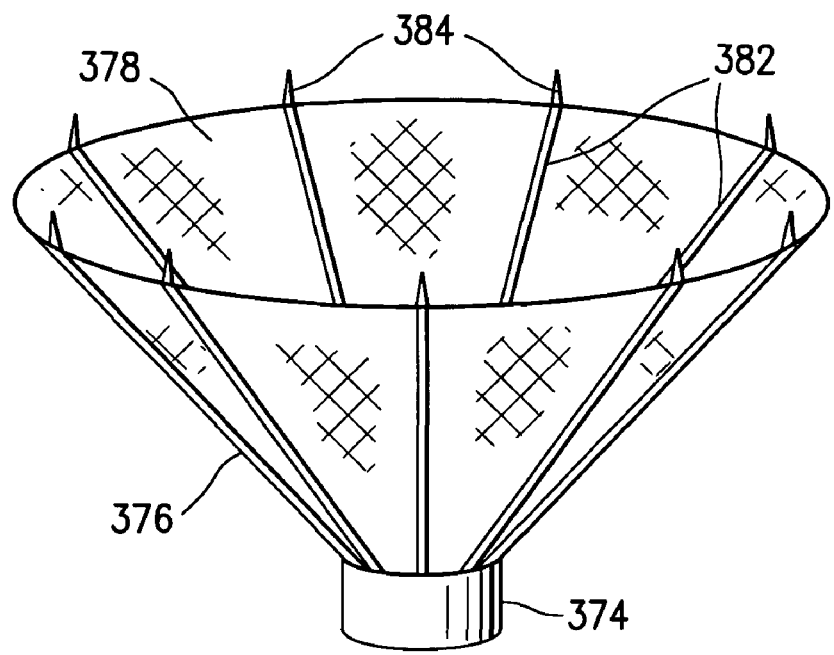
FIG. 20A is a perspective view of a frame of a cardiac device according to another embodiment of the invention.
Figure 20B:
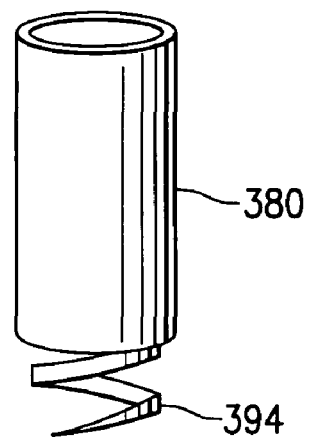
FIG. 20B is a perspective view of a stem of the cardiac device of FIG. 20A.
Figure 20C:
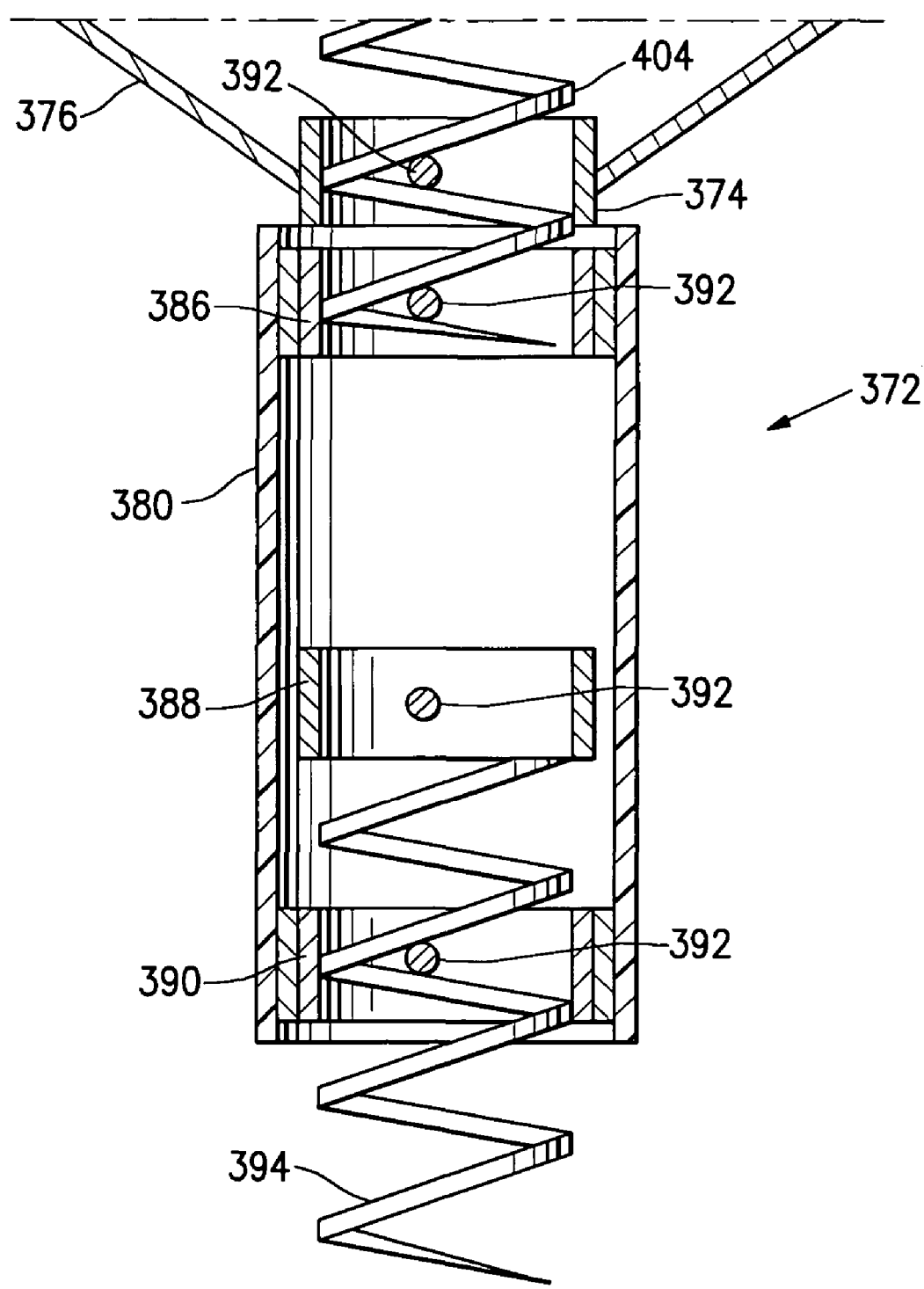
FIG. 20C is a cross-sectional side view of the cardiac device of FIG. 20A and FIG. 20B with the stem attached to the frame.

FIGS. 20A, 20B, and 20C illustrate a cardiac device 372 according to a further embodiment of the invention. The cardiac device 372 includes a frame hub 374, a frame 376, a membrane 378, and a stem 380. The frame hub 374 lies at a central portion of the frame 376. The frame 376 includes a plurality of segments 382 which extend radially and upwardly from the frame hub 374. A sharp passive anchor 384 lies at the end of each of the segments 382. The membrane 378 is stretched between the segments 382 to form a cone-shaped body. Before installation, the stem 380 is unattached to the frame hub 374 and includes a proximal hub 386, an anchor hub 388, and a distal hub 390, each having a pin 392 extending across an inner surface thereof, similar to that of the frame hub 190. The proximal 386 and distal 390 hubs are frictionally held near their respective ends in the stem 380, and the anchor hub 388 is loose within the stem 380 so that it may move. An active anchor 394 extends downwards from the anchor hub 388.

Figure 20D:
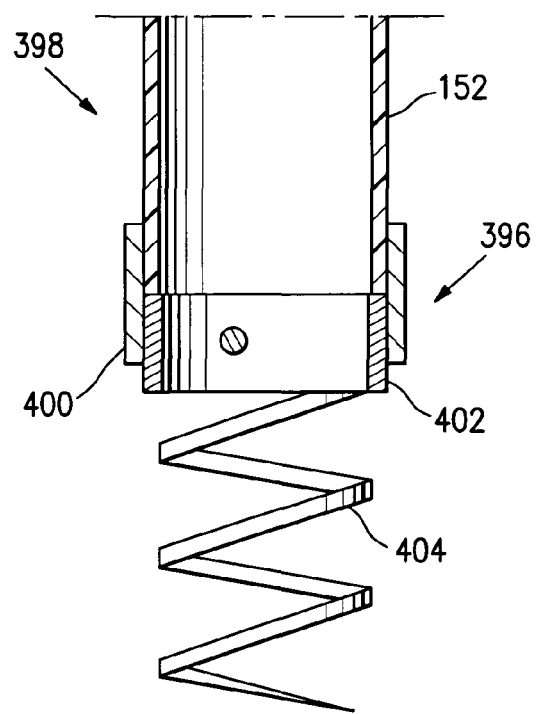
FIG. 20D is a cross-sectional side view of a distal end of a deployment member of a deployment mechanism according to another embodiment of the invention.
Figure 20E:
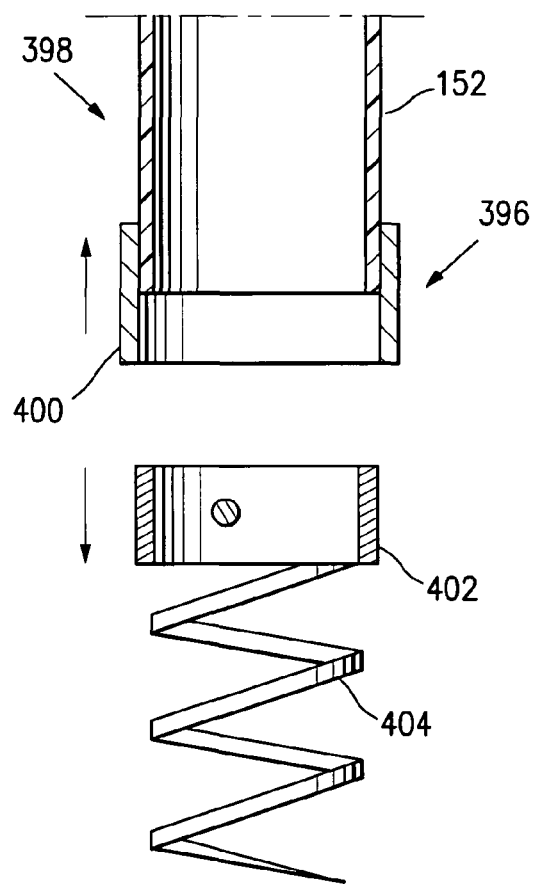
FIG. 20E is a cross-sectional side view of the distal end of the deployment member of a deployment mechanism of FIG. 20D.

FIGS. 20D and 20E illustrate another embodiment of a distal end 396 of a deployment member 398. The distal end 396 includes a detachment piece 400 and an attachment hub 402. The detachment piece 400 has been added to the distal end of the outer torque shaft 152. The detachment piece 400 is a ring shaped body made of stainless steel with a length of 3 mm and an inner diameter suitable to frictionally hold the attachment hub 402, which is similar to the frame hub 190. An attachment screw 404, similar to the detachment screw 164, extends downwards from the attachment hub 402. Referring specifically to FIG. 20E, forces along the length of the deployment member 398 will, by design, cause the attachment hub 402 to become dislodged from the detachment piece 400.

Figure 20F:
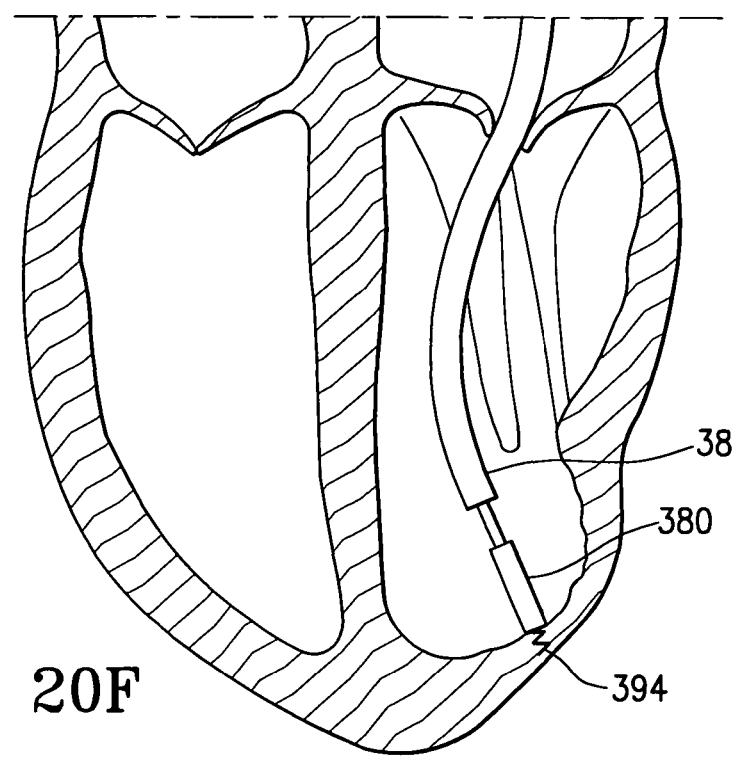
FIGS. 20F-20I are cross sectional side views of a human heart illustrating installation of the cardiac device of FIG. 20A and FIG. 20B.
Figure 20G:
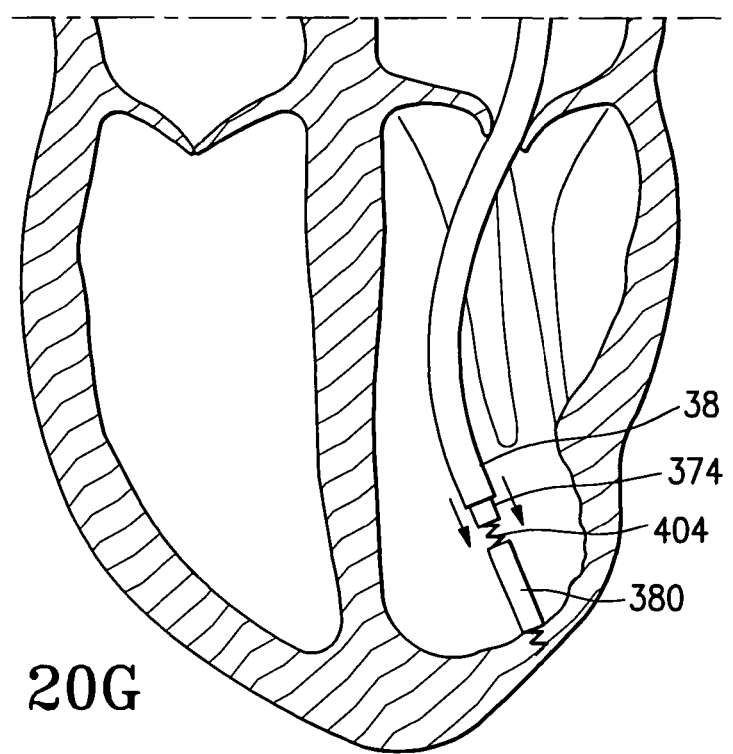
Figure 20H:
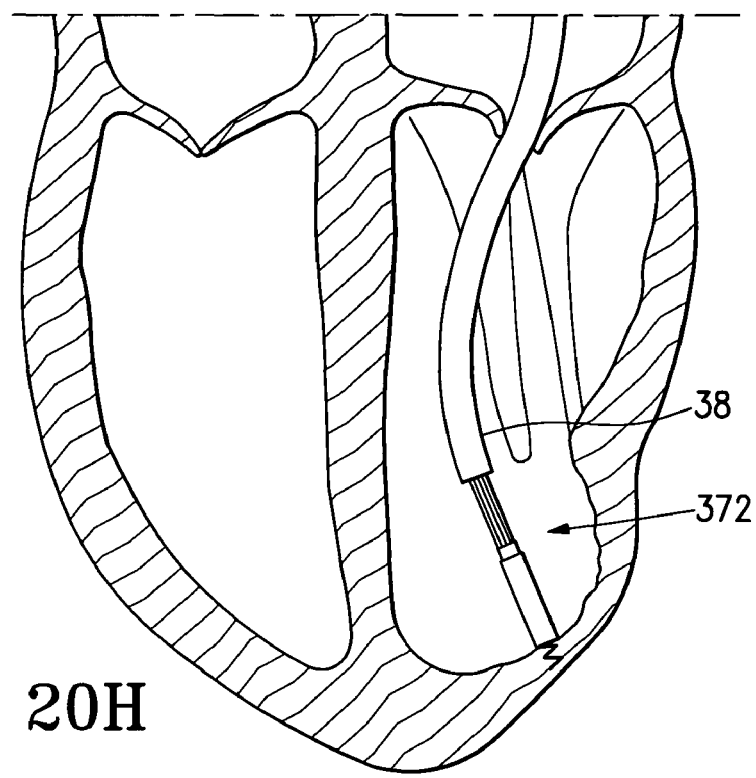

FIGS. 20F-20H illustrate installation of the cardiac device 372 of FIGS. 20A and 20B into a human heart. In this embodiment, the deployment member used does not include the securing mechanism 166 so that the inner and outer torque shafts may move axially relative to one another.

Before the device 372 and stem 380 are inserted into a heart, the inner torque shaft is passed through the frame hub 374, the proximal hub 386, and the anchor hub 388, and the outer torque shaft is positioned and rotated so that the attachment screw 404 engages both the pins 392 of the frame 374 and proximal 386 hubs, securing the cardiac device 372 to the stem 380. The device 372 and the stem 380 are then retracted into the catheter 38 and steered into a left ventricle. The stem 380 is secured to an apex of an akinetic portion of a left ventricle of the heart by rotating the inner torque shaft, causing the active anchor 394 to penetrate the myocardium. Rotation of the outer torque shaft then causes the attachment screw 404 to disengage the pin 392 of the proximal hub 386, and the device 372 is released from the stem 380. However, the inner torque shaft remains engaged with the hubs in the stem 380.

Figure 20I:
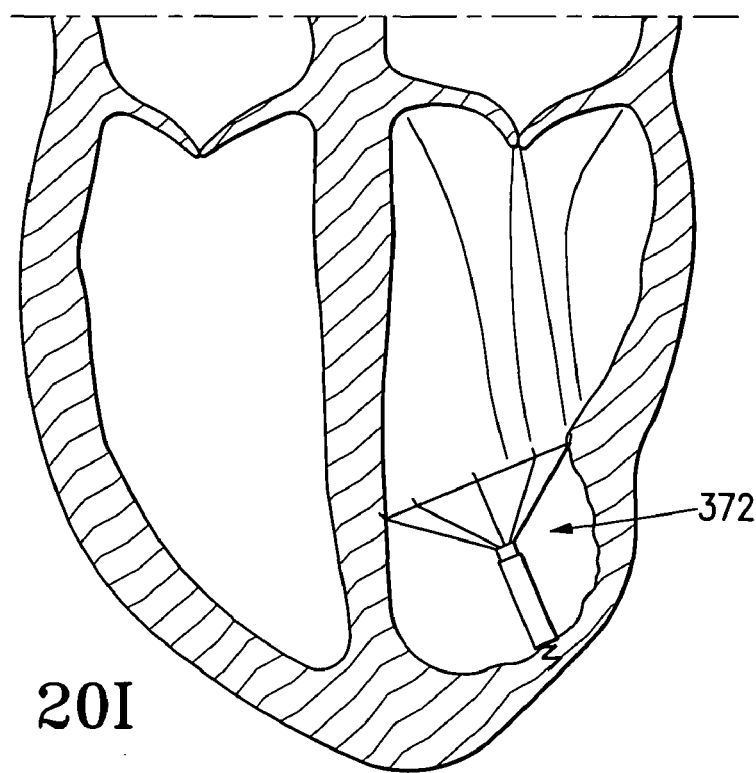

If it is determined that the stem 380 has been properly positioned, the cardiac device 372, secured to the outer torque shaft, is pushed over the inner torque shaft to meet the stem 380. The outer torque shaft is again rotated so that the attachment screw 404 reengages the pin 392 on the proximal hub 386 of the stem, thus re-securing the stem 380 to the frame 376. The deployment member 398 is then forcibly pulled away from the device 372 and the detachment piece 400 releases the attachment screw 404. FIG. 20I illustrates the human heart with the cardiac device 372 of FIGS. 20A and 20B installed.

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed:

1. A device for improving a patient's cardiac function, comprising:
   a. a collapsible and expandable frame having first and second portions, the frame being insertable into a ventricle of the patient's heart when collapsed, when expanded to a diameter equal or greater than 35 mm and less than or equal to 100 mm the frame being in a selected position in the ventricle and the second portion of the frame covering a wall in the ventricle;
   b. a membrane secured to the frame such that the membrane divides the ventricle into at least a main productive portion and a non-productive portion when the frame is expanded, the frame and the membrane jointly forming a cardiac device; and
   c. an anchor connected to the cardiac device, the anchor being insertable into the patient's heart tissue to secure the cardiac device in the selected position in the ventricle, wherein all portions of the frame secured to the membrane, when expanded, are at a minimum angle of 10° to 45° with respect to a longitudinal axis of the anchor.

* * * * *